United States Patent [19]

Furuya et al.

[11] Patent Number: 5,654,309
[45] Date of Patent: Aug. 5, 1997

[54] PYRIDOPYRIMIDINE DERIVATIVES, THEIR PRODUCTION AND USE

[75] Inventors: Shuichi Furuya; Tetsuya Ohtaki, both of Tsukuba, Japan

[73] Assignee: Takeda Chemical Industries, Ltd., Osaka, Japan

[21] Appl. No.: 480,862

[22] Filed: Jun. 7, 1995

Related U.S. Application Data

[63] Continuation of Ser. No. 175,107, Dec. 29, 1993, abandoned

[30] Foreign Application Priority Data

Dec. 29, 1992 [JP] Japan .................. 4-360384
Nov. 5, 1993 [JP] Japan .................. 5-277136

[51] Int. Cl.⁶ .................. C07D 471/04; C07D 239/545; C07D 471/22; A61K 31/505
[52] U.S. Cl. .................. 514/258; 544/279; 544/245; 544/311
[58] Field of Search .................. 544/279; 514/258

[56] References Cited

U.S. PATENT DOCUMENTS 3,984,415 10/1976 Noda .................. 544/279

FOREIGN PATENT DOCUMENTS

| | | |
|---|---|---|
| 510526 | 10/1992 | European Pat. Off. |
| 3601731 | 7/1987 | Germany |
| 50-142596 | 11/1975 | Japan |
| 9212979 | 8/1992 | WIPO |

OTHER PUBLICATIONS

Kiowski *The Lancet* 346, p. 732 (1995).
Clozel, J. Pharm. Exp. Ther. 270, 228 (1994).
Koseki, Am. J. Physiology, 256, R858–R866 (1989).
Watanake, Circulation Research 69, 370 (1991).
Shibouta, Life Sci. 46, 1611 (1990).
Kanno, J. A.M.A 264, 2868 (1990).
Aramori, Molec. Pharm 43, 127 (1994).
Clozel II, J Cardiovasc. Pharmacology, 22 (Suppl. 8) 5377 (1993).
Mihara, Eur. J. Pharmacology—Molec. Pharmacology Section 246, 33–38 (1993).
Ihara, Life Sciences 50, 247–255 (1991).
Nirei, Life Sciences 52, 1869 (1993).
Doherty, J. Med. Chem 35(9), 1493 (1992).
Clozel J. *Nature*, 365, p. 759 (Oct. 1993).

*Primary Examiner*—Mark L. Berch
*Attorney, Agent, or Firm*—Foley & Lardner

[57] ABSTRACT

Pyridopyrimidine derivatives of the formula (A), wherein n denotes an integer of 0 to 3, Q stands for $-(CH_2)_m-$, $-O-$, $-S(O)_P-$ or $-N-$, and $R^1$ to $R^5$ stand for substituents, where $R^3$ is an optionally substituted phenyl, naphthyl, pyridyl, quinolyl, quinolonyl, or thienyl group; or its salt are described. Preparation and use of the derivatives for an antagonistic agent for an endothelin receptor are shown. An endothelin receptor antagonist including the derivative is effective as a therapeutic composition of acute renal insufficiency, myocardial infarction, hypertension, cerebral infarction, angina pectoris, arteriosclerosis, hepatopathy, pulmonary hypertension, bronchial asthma, organohypofunction occurring during operation of transplantation of organs.

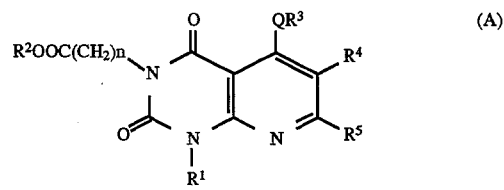

(A)

13 Claims, No Drawings

PYRIDOPYRIMIDINE DERIVATIVES, THEIR PRODUCTION AND USE

This application is a continuation of application Ser. No. 08/175,107, filed Dec. 29, 1993, abandoned.

FIELD OF THE INVENTION

This invention relates to novel compounds having condensed heterocyclic ring, which have excellent activities as medicines, i.e. endothelin receptor antagonistic activities, and are useful as vasodilators and therapeutic composition of such diseases as hypertension, acute renal insufficiency, myocardial infarction, angina pectoris and cerebral angiospasm, and a method of producing these compounds.

DESCRIPTION OF THE PRIOR ART

It has been suggested that, among adult diseases increasing in recent years, for example cerebral infarction, angina pectoris, myocardial infarction and renal insufficiency which are caused by ischemia are possibly concerned with endothelin. Endothelin is a peptide consisting of 21 amino acids produced from endothelial cells, and it is obtained as endothelin-1, endothelin-2 and endothelin-3. Hereinafter, in this specification, these endothelin groups are combinedly called "endothelin". It has been reported that endothelin has, among in vivo or synthetic substances which have so far been found, most potent and long-lasting vasoconstrictive action, pressor activity and action of enhancing heart muscle contraction activity. It is considered that the actions of these peptides are performed via endothelin receptor which is considered to exist on smooth muscle membrane of blood vessels etc. As endothelin receptors, have been known endothelin-A receptor and endothelin-B receptor (hereinafter collectively called "endothelin receptor").

Therefore, compounds showing affinity for endothelin receptor while showing endothelin receptor antagonistic activity have prophylactic and therapeutic effects against diseases caused by ischemia, for example, cerebral infarction, angina pectoris, myocardial infarction and renal insufficiency, thus development of these compounds being greatly expected.

As endothelin receptor antagonistic substances, compounds derived from natural source have been obtained, as disclosed in several researchers, for example, Ishimaru et al. [JPA H4(1992)-134048], Fujimoto et al. [Federation of European Biochemical Societies Letters, 305 p.41 (1992)], Oh-hata et al. [JPA H3(1991)-047163], Miyata et al. [JPA H4(1992)-046127] and Yano et al. [JPA H3(1991)-094692].

Further, reports were made by Henmi et al. [EP 457195-A2], Ishikawa et al. [EP 460679-A2 and EP 436189-A], Hashimoto et al. [JPA H3(1992)-130299], Masaki et al. [JPA H3(1992)-024099], G. Hamon et al. [EP 487410-A2], W. L. Cody et al [J. Med. Chem., (1992) 35, p. 3303] and Wakimasu et al. [WO9113089-A, EP499266-A1], that peptide compounds were obtained.

However, when dosage forms of drugs, stability of compounds, durability of pharmacological actions and stability to metabolism are taken into consideration, synthetic endothelin receptor antagonists prepared by non-peptidizing these peptide compounds are strongly desired. Under the present circumstances, however, very few reports are found on non-peptide synthetic endothelin receptor antagonists, for example, a recent report by K. Bali et al. [EP510526-A1].

On the other hand, a 2,4(1H,3H)-dioxopyrido[2,3-d]pyrimidine-8-acetic acid derivative was reported by H. R. Haward et al. [WO92/12979], which has relatively similar structure to the compound of present invention. The substituents of these compounds, however, are apparently different from those of the present invention. Furthermore, it is reported that the former compounds are useful in therapy as aldose reductase inhibitors for the control of certain chronic diabetic complications but have no actions as endothelin receptor antagonists.

SUMMARY OF THE INVENTION

It is an object of the present invention to provide novel and useful compounds each having a condensed heterocyclic ring, especially novel compounds which can be used as non-peptide synthetic endothelin receptor antagonists, wherby the foregoing problems can be overcome.

It is another object of the present invention to provide a novel compound having endothelin receptor antagonistic properties which is stable as compound and has long-lasting pharmacological properties and metabolic stability.

It is a further object of the present invention to provide a method of producing the compound and an endothelin receptor antagonistic composition.

DETAILED DESCRIPTION OF THE PREFERRED EMBODIMENT

The present inventors have conducted diligent research works to attain the above objects, resulting in finding out that these objects can be achieved by novel pyridopyrimidine derivatives having endothelin receptor antagonistic activities, and thus the present invention has been accomplished based on this finding.

The present invention provides a pyrido[2,3-d]pyrimidine derivative of the formula (A) or a salt thereof;

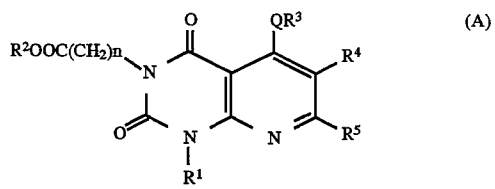

wherein Q is $-(CH_2)_m-$ (m denotes 0 or an integer of 1 to 2), $-O-$, $-S(O)_p-$ (p denotes 0 or an integer of 1 to 2) or $-NH-$, and n denotes 0 or an integer of 1 to 3; $R^1$ and $R^2$ independently are hydrogen atom, an optionally substituted $C_{1-6}$ alkyl group, an optionally substituted aryl group or an optionally substituted aralkyl group; $R^3$ is an optionally substituted cyclic hydrocarbon group or an optionally substituted heterocyclic group; $R^4$ is hydrogen atom, an optionally substituted $C_{1-6}$ alkyl group, an optionally substituted aryl group or an optionally substituted aralkyl group, cyano group, $-COOR^6$ ($R^6$ is hydrogen atom, an optionally substituted $C_{1-6}$ alkyl group, an optionally substituted cyclic hydrocarbon group or an optionally substituted aralkyl group) or $-CONR^7R^8$ ($R^7$ and $R^8$ independently are hydrogen atom, an optionally substituted $C_{1-6}$ alkyl group, an optionally substituted cyclic hydrocarbon group or an optionally substituted aralkyl group); $R^5$ is hydrogen atom, an optionally substituted $C_{1-6}$ alkyl group, an optionally substituted aryl group, an optionally substituted aralkyl group, $-X^1R^9$ ($X^1$ is $-O-$, $-NR^{10}-$ or $-S-$, $R^9$ and $R^{10}$ independently are hydrogen atom, an optionally substituted $C_{1-6}$ alkyl group, an optionally substituted aryl group or an optionally substituted aralkyl group).

As especially preferable examples of the pyridopyrimidine derivative and its salt of this invention, mention is made of the derivative being represented by the following general formula (A') and a salt thereof;

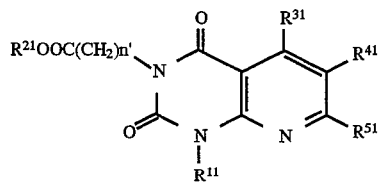

wherein n' denotes an integer of 1 to 3; $R^{11}$ is hydrogen atom, a $C_{1-6}$ alkyl group, or a $C_{7-15}$ aralkyl group optionally substituted by a $C_{1-6}$ alkoxy group or $C_{-6}$ alkylthio group; $R^{21}$ is hydrogen atom or a $C_{1-6}$ alkyl group; $R^{31}$ is a $C_{6-15}$ aryl group optionally substituted by at least one group selected from the group consisting of a $C_{1-6}$ alkyl group, a $C_{3-7}$ cycloalkyl group, a $C_{1-6}$ alkoxy group, a halogen atom, nitro group, cyano group and phenyl group, or a 5 to 13-membered aromatic heterocyclic group containing 1 to 4 hetero atoms selected from nitrogen atom, oxygen atom and sulfur atom optionally substituted by at least one group selected from the group consisting of a $C_{1-6}$ alkyl group, a $C_{1-6}$ alkoxy group, oxo group and hydroxyl group; $R^{41}$ is —$COOR^{51}$ ($R^{51}$ is hydrogen atom; a $C_{1-6}$ alkyl group optionally substituted by carboxyl group or a 5 to 10-membered heterocyclic group containing 1 to 4 hetero atoms selected from nitrogen atom, oxygen atom and sulfur atom; $C_{3-7}$ cycloalkyl group; or $C_{6-15}$ aralkyl group) or —$CONR^{71}R^{81}$ ($R^{71}$ and $R^{81}$ independently are hydrogen atom, $C_{1-6}$ alkyl group, or $C_{6-14}$ aryl group); $R^{51}$ is hydrogen atom, a $C_{1-6}$ alkyl group, or a $C_{6-14}$ aryl group optionally substituted by a $C_{1-3}$ alkylenedioxy group.

The present invention is to provide a process for producing a pyrido[2,3-d]pyrimidine derivative represented by the formula (A) or a salt thereof, which comprises subjecting a compound represented by the formula (I);

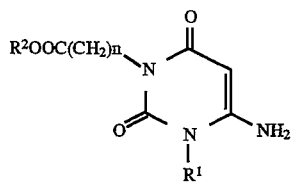

wherein n, $R^1$ and $R^2$ are of the same meaning as defined above] or a salt thereof to heating under reflux in a solvent together with a cyclic hydrocarbon or heterocyclic aldehyde represented by the formula $R^3Q$—CHO (Q and $R^3$ are of the same meaning as defined above) and beta-ketoester, or together with a derivative obtained by subjecting the said aldehyde and ketoester to dehydrative condensation, to give a compound of the formula (B);

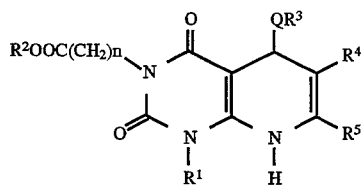

wherein n, Q, $R^1$, $R^2$, $R^3$, $R^4$ and $R^5$ are of the same meaning as defined above, or a salt thereof, subjecting the compound (B) or a salt thereof to oxidation with an oxidizing agent to give a compound of the formula (A);

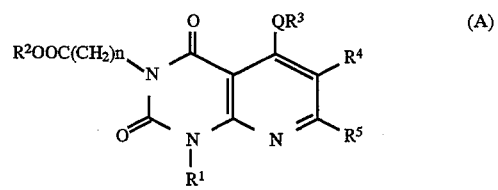

wherein n, Q, $R^1$, $R^2$, $R^3$, $R^4$ and $R^5$ are of the same meaning as defined above, or a salt thereof. Further in the case where $R^2$ is not a hydrogen atom, the said compound (A) or a salt thereof may be hydrolyzed to give a compound of the formula (Aa)

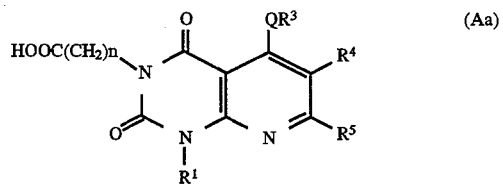

wherein n, $R^1$, $R^3$, $R^4$, $R^5$ and Q are of the same meaning as defined above, or a salt thereof.

Further, the present invention is to provide a process for producing a pyrido[2,3-d]pyrimidine derivative represented by the above-mentioned formula (A) or a salt thereof, which comprises subjecting a compound represented by the formula (I)

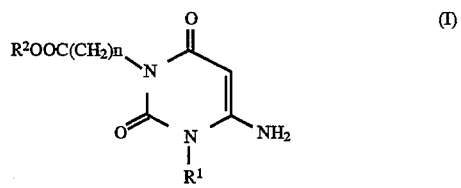

wherein n, $R^1$ and $R^2$ are of the same meaning as defined above, to heating together with a 3,3-bismethylthio derivative in dimethylformamide to give a compound of the formula (C)

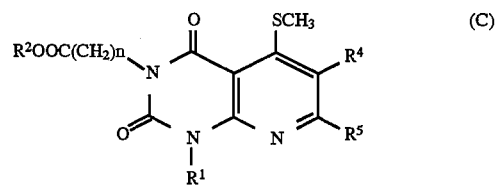

wherein n, $R^1$, $R^2$, $R^4$ and $R^5$ are of the same meaning as defined above, or a salt thereof, allowing the compound (C) or a salt thereof to react with a nucleophilic reagent represented by the formula $R^3QH$ (Q and $R^3$ are of the same meaning as defined above) to give a compound of the formula (A);

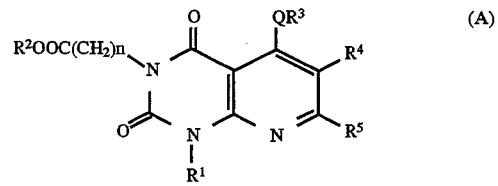

wherein n, Q, $R^1$, $R^2$, $R^3$, $R^4$ and $R^5$ are of the same meaning as defined above, or a salt thereof. Further in the case where $R^2$ is not a hydrogen atom, the said compound (A) or a salt thereof may be hydrolyzed to give a compound of the formula (Aa);

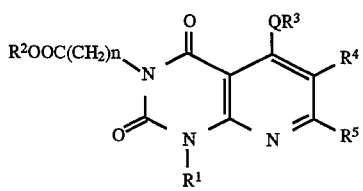

(Aa)

wherein n, $R^1$, $R^3$, $R^4$, $R^5$ and Q are of the same meaning as defined above, or a salt thereof.

Further, the present invention is to provide a process for producing a pyrido[2,3-d]pyrimidine derivative represented by the above formula (A) or a salt thereof, which comprises subjecting a compound represented by the formula (II);

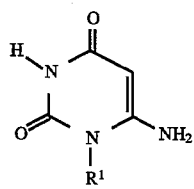

(II)

wherein $R^1$ is of the same meaning as defined above or a salt thereof to heating under reflux in a solvent together with a derivative represented by the formula $QR^3CHCR^4COR^5$ (Q, $R^3$, $R^4$ and $R^5$ are of the same meaning as defined above) obtained by subjecting a cyclic hydrocarbon or heterocyclic aldehyde represented by the formula $R^3Q$—CHO (Q and $R^3$ are of the same meaning as defined above) and beta-ketoester to dehydrative condensation, to give a compound of the formula (B');

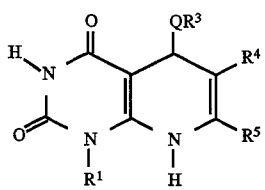

(B')

wherein Q, $R^1$, $R^3$, $R^4$ and $R^5$ are of the same meaning as defined above, or a salt thereof, subjecting the compound (B') or a salt thereof to oxidation with an oxidizing agent to give a compound of the formula (D);

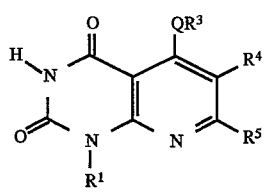

(D)

wherein Q, $R^1$, $R^3$, $R^4$ and $R^5$ are of the same meaning as defined above; then subjecting the compound (D) or a salt thereof to reacting with a halogenated alkylcarboxylate derivative represented by the formula $X^2(CH_2)_nCOOR^2$, wherein $X^2$ is a halogen atom, n and $R^2$ are of the same meaning as defined above, in an appropriate solvent, in the presence of a base to give a compound of the formula (A) and a salt thereof. Further, in the case where $R^2$ is not a hydrogen atom, the said compound (A) or a salt thereof may be hydrolyzed to give a compound of the formula (Aa) or a salt thereof.

Further, the present invention is to provide a process for producing a pyrido[2,3-d]pyrimidine derivative represented by the above-mentioned general formula (A) or a salt thereof wherein $QR^3$ is 2-(4-quinolonyl) group and $R^4$ is carboxyl group, which comprises heating a compound or its salt, the compound being represented by the formula (E);

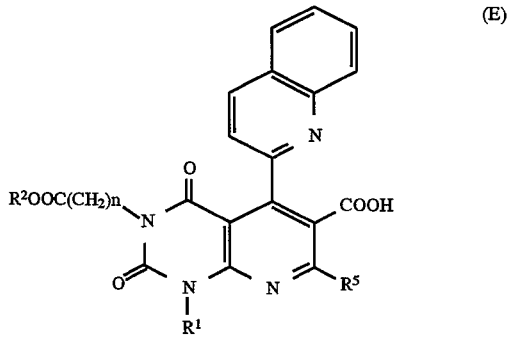

(E)

wherein n, Q, $R^1$, $R^2$ and $R^5$ are of the same meaning as defined above, under reflux in a solvent together with thionyl chloride, to give a compound of the formula (Ab);

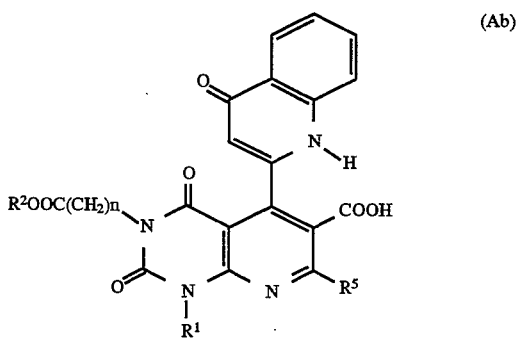

(Ab)

wherein n, Q, $R^1$, $R^2$ and $R^5$ are of the same meaning as defined above, or a salt thereof.

Further, in the case where $R^2$ is not a hydrogen atom, the said compound (Ab) or a salt thereof may be hydrolyzed to give a compound of the formula (Ac) or a salt thereof;

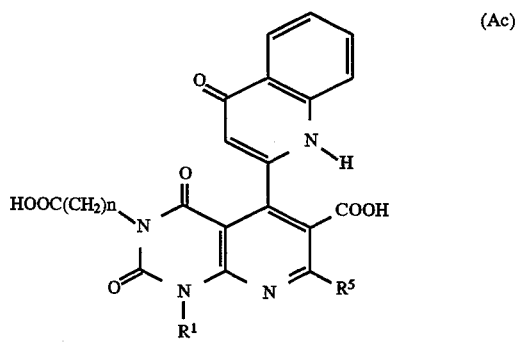

(Ac)

wherein n, $R^1$ and $R^5$ are of the same meaning as defined above.

Further, the present invention is to provide a process for producing a pyrido[2,3-d]pyrimidine derivative represented by the above-mentioned general formula (A) or a salt thereof, which comprises reacting a compound or its salt, the compound being represented by the formula (F);

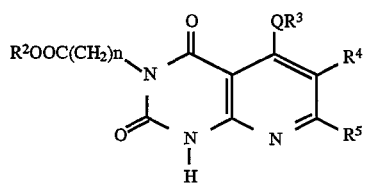

(F)

wherein n, Q, $R^2$, $R^3$, $R^4$ and $R^5$ are of the same meaning as defined above, with a halogenated alkyl, halogenated aryl or halogenated aralkyl compound represented by the formula $R^1X^2$ wherein $X^2$ is a halogen atom, and $R^1$ is of the same meaning as defined above, in an appropriate solvent, in the presence of a base to give a compound of the formula (A) and a salt thereof. Further, in the case where $R^2$ is not a hydrogen atom, the said compound (A) or a salt thereof may be hydrolyzed to give a compound of the formula (Aa) or a salt thereof.

Further, the present invention is to provide a process for producing a pyrido[2,3-d]pyrimidine derivative represented by the above-mentioned formula (A) or a salt thereof, wherein $R^4$ is —COOR$^{6'}$ ($R^{6'}$ is an optionally substituted $C_{1-6}$ alkyl group, an optionally substituted cyclic hydrocarbon group or an optionally substituted aralkyl group, which comprises reacting a compound or its salt, the compound being represented by the formula (G);

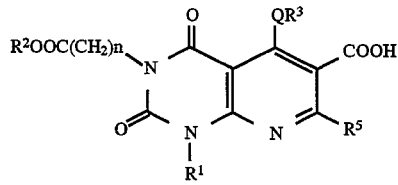

(G)

wherein n, Q, $R^1$, $R^2$, $R^3$ and $R^5$ are of the same meaning as defined above, with a halogenated alkyl, a halogenated aryl or halogenated aralkyl compound represented by the formula $R^{6'}X^2$ wherein $X^2$ is halogen atom, and $R^{6'}$ is of the same meaning as defined above, in appropriate solvent, in the presence of a base to give a compound of the formula (A), wherein $R^4$ is —COOR$^{6'}$ ($R^{6'}$ is of the same meaning as defined above) and a salt thereof. Further, in the case where $R^2$ is not a hydrogen atom, the said compound (A) or a salt thereof may be hydrolyzed to give a compound of the formula (Aa) wherein $R^4$ is —COOR$^{6'}$ ($R^{6'}$ is of the same meaning as defined above) or a salt thereof.

Further, the present invention is to provide a process for producing a pyrido[2,3-d]pyrimidine derivative represented by the above-mentioned general formula (A) wherein QR$^3$ is 2-(4-quinolonyl) group and $R^4$ is —COOR$^6$ or —CONR$^7$R$^8$ ($R^6$, $R^7$ and $R^8$ are of the same meaning as defined above) or a salt thereof, which comprises reacting a compound or its salt, the compound being represented by the formula (Ad);

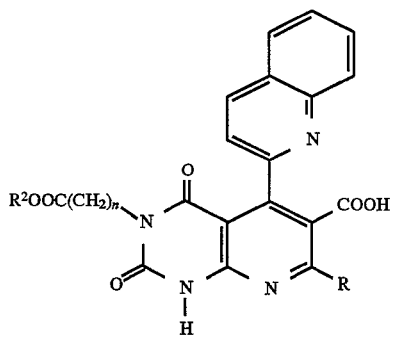

(Ad)

wherein n, $R^2$ and $R^5$ are of the same meaning as defined above, with thionyl chloride in an appropriate solvent, then reacting with a halogenated alkyl, halogenated aryl or halogenated aralkyl compound represented by the formula $R^1X^2$, wherein $X^2$ is a halogen atom, and $R^1$ is of the same meaning as defined above, in an appropriate solvent, in the presence of a base to give a compound of the formula (H)

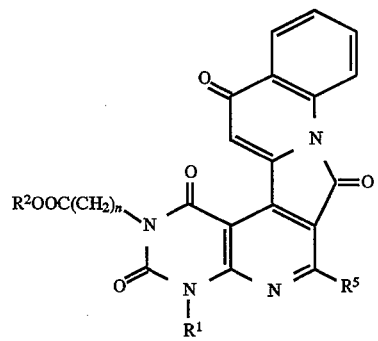

(H)

wherein n, $R^1$, $R^2$ and $R^5$ are of the same meaning as defined above, or a salt thereof; and then subjecting the compound (H) or a salt thereof to reacting with a nucleophilic reagent, which is capable of incorporating thereinto a substituent represented by —OR$^6$ or —NR$^7$R$^8$ ($R^6$, $R^7$ and $R^8$ is of the same meaning as defined above), in an appropriate solvent to give a compound of the formula (A) wherein QR$^3$ is 2-(4-quinolonyl) group and $R^4$ is —COOR$^6$ or —CONR$^7$R$^8$ ($R^6$, $R^7$ and $R^8$ are of the same meaning as defined above) and a salt thereof.

Further, in the case where $R^2$ is not a hydrogen atom, the said compound (A) or a salt thereof may be hydrolyzed to give a compound of the formula (Ac) wherein QR$^3$ is 2-(4-quinolonyl) group and $R^4$ is —COOR$^6$ or —CONR$^7$R$^8$ ($R^6$, $R^7$ and $R^8$ is of the same meaning as defined above) or a salt thereof.

And, the present invention is to provide an endothelin receptor antagonistic agent containing, as the effective component, a pyrido[2,3-d]pyrimidine derivative represented by the above-mentioned formula (A) or a pharmaceutically acceptable salt thereof.

Furthr the present invention is to provide said endothelin receptor antagonistic composition as a therapeutic composition of acute renal insufficiency, myocardial infarction, hypertension, cerebral infarction, angina pectoris, arterial sclerosis, hepatopathy, pulmonary hypertension, bronchial asthma, organohypofunction occuring during operation or transplantation of organs, especially a therapeutic composition of acute renal insufficiency and/or myocardial infarction.

The compound represented by the formula (A) of this invention (hereinafter referred to as compound [A]) will be described in further detail.

In the formula (A), Q means —$(CH_2)_m$— (m means 0 or an integer of 1 to 2), —O—, —$S(O)_p$— (p means 0 or an integer of 1 to 2) or —NH—. Preferably, Q is —$(CH_2)_m$—, especially preferably m is 0 or 1.

The symbol n means 0 or an integer of 1 to 3, preferably n is 1 or 2, especially preferably n is 1.

In the formula (A), $R^1$ and $R^2$ may be the same as or different from each other, and respectively are hydrogen atom, an optionally substituted $C_{1-6}$ alkyl group, an optionally substituted aryl group or an optionally substituted aralkyl group.

Examples of the $C_{1-6}$ alkyl group include methyl group, ethyl group, propyl group, isopropyl group, butyl group, isobutyl group, sec-butyl group, tert-butyl group, pentyl group, isopentyl group, neopentyl group, tert-pentyl group, 1-ethylpropyl group, hexyl group, isohexyl group, 1,1-dimethylbutyl group, 2,2-dimethylbutyl group, 3,3-dimethylbutyl group and 2-ethylbutyl group.

Among them, $C_{1-4}$ alkyl groups as exemplified by methyl group, ethyl group, propyl group, isopropyl group, butyl group and isobutyl group, for example, are preferable. Methyl group is especially preferable.

The $C_{1-6}$ alkyl group may have 1 to 3 appropriate substituents, as exemplified by a $C_{3-7}$ cycloalkyl group, a 5 to 10-membered aromatic heterocyclic group containing 1 to 4 hereto atoms selected from nitrogen atom, oxygen atom and sulfur atom, a 5 to 10-membered non-aromatic heterocyclic group containing 1 to 4 hetero atoms selected from nitrogen atom, oxygen atom and sulfur atom, amino group, a mono-($C_{1-6}$ alkyl)amino group, a di($C_{1-6}$ alkyl)amino group, amidino group, a $C_{1-6}$ alkylcarbonyl group, a $C_{6-14}$ arylcarbonyl group, a $C_{7-15}$ aralkylcarbonyl group, a $C_{1-6}$ alkoxycarbonyl group, a $C_{6-14}$ aryloxycarbonyl group, a $C_{7-15}$ aralkyloxycarbonyl group, carbamoyl group, a mono-($C_{1-6}$)alkylcarbamoyl group, a di-($C_{1-6}$)alkylcarbamoyl group, sulfamoyl group, a mono-($C_{1-6}$)alkylsulfamoyl group, a di-($C_{1-6}$)alkylsulfamoyl group, carboxyl group, hydroxyl group, a $C_{1-6}$ alkoxy group, a $C_{2-6}$ alkenyloxy group, a $C_{3-7}$ cycloalkyloxy group, a $C_{6-14}$ aryloxy group, a $C_{7-15}$ aralkyloxy group, mercapto group, a $C_{1-6}$ alkylthio group, a $C_{6-14}$ arylthio group, a $C_{7-15}$ aralkylthio group, sulfo group, cyano group, azido group, nitro group, nitroso group or a halogen atom.

In the present invention, the aryl group means monocyclic or condensed polycyclic aromatic hydrocarbon groups, as exemplified by $C_{6-14}$ aryl group such as phenyl group, naphthyl group, anthryl group, phenanthryl group and acenaphthylenyl group, especially preferable ones being phenyl group, 1-naphthyl group and 2-naphthyl group.

The aryl group may have one or more, preferably 1 to 3 appropriate substituents, as exemplified by a $C_{1-6}$ alkyl group (e.g. methyl group, ethyl group and propyl group), $C_{2-6}$ alkenyl group (e.g. vinyl group, allyl group and 2-butenyl group), $C_{2-6}$ alkynyl group (e.g. propargyl group and 2-butynyl group), a cycloalkyl group (e.g. a $C_{3-7}$ cycloalkyl group such as cyclopropyl group, cyclobutyl group, cyclopentyl group and cyclohexyl group), $C_{6-14}$ aryl group (e.g. phenyl group and naphthyl group), aromatic heterocyclic group (e.g. a 5 to 9-membered aromatic heterocyclic group containing 1 to 4 hetero atoms selected from nitrogen atom, oxygen atom and sulfur atom, as exemplified by furyl group, thienyl group, pyrrolyl group, thiazolyl group, imidazolyl group, pyrazolyl group, pyridyl group, quinolyl group and quinolonyl group), non-aromatic heterocyclic group (e.g. a 5 to 9-membered non-aromatic heterocyclic group containing 1 to 4 hetero atoms selected from nitrogen atom, oxygen atom and sulfur atom, as exemplified by oxiranyl group, azetidinyl group, oxetanyl group, thiethanyl group, pyrrolidinyl group, teterahydrofuryl group, thiolanyl group, piperidyl group, tetrahydropyranyl group, morphonyl group, thiomorphonyl group and piperazinyl group), aralkyl group (e.g. a $C_{7-15}$ aralkyl group such as benzyl group, phenylethyl group, 1-naphtylmethyl, 1-naphthylethyl), amino group, N-monosubstituted amino group (e.g. $C_{1-6}$ monoalkylamino group such as methylamino group, ethylamino group and propylamino group), N,N-disubstituted amino group (e.g. N,N-disubstituted amino group substituted with a $C_{1-6}$ alkyl group, as exemplified by dimethyl amino group and diethylamino group), amidino group, acyl group (e.g. a $C_{1-8}$ alkylcarbonyl group such as formyl group, acetyl group, propionyl group and butyryl group; a $C_{6-14}$ arylcarbonyl group such as benzoyl group; a $C_{7-15}$ aralkylcarbonyl group such as benzylcarbonyl group, phenylethylcarbonyl group, a $C_{1-8}$ alkoxycarbonyl group such as methoxycarbonyl group and ethoxycarbonyl group; a $C_{6-14}$ aryloxycarbonyl group such as phenyloxycarbonyl group alpha-naphthylcarbonyl group and a $C_{7-15}$ aralkyloxycarbonyl group such as benzyloxycarbonyl group, 1-naphthyloxycarbonyl group), carbamoyl group, N-monosubstituted carbamoyl group (e.g. a $C_{1-6}$ alkylcarbamoyl group such as methylcarbamoyl group, ethylcarbamoyl group and propylcarbamoyl group), N,N-disubstituted carbamoyl group (e.g. N,N-disubstituted carbamoyl group substituted with a $C_{1-6}$ alkyl group, as exemplified by dimethylcarbamoyl group and diethylcarbamoyl group), sulfamoyl group, N-monosubstituted sulfamoyl group (e.g. N-alkylsulfamoyl group having a $C_{1-6}$ alkyl group, as exemplified by methylsulfamoyl group, ethylsulfamoyl group and propylsulfamoyl group), N,N-disubstituted sulfamoyl group (e.g. N,N-dialkyl substituted sulfamoyl group having a $C_{1-6}$ alkyl group, as exemplified by dimethylsulfamoyl group and diethylsulfamoyl group), carboxyl group, hydroxyl group, a $C_{1-6}$ alkxoy group (e.g. methoxy group, ethoxy group and propoxy group), a $C_{2-6}$ alkenyloxy group (e.g. vinyloxy group and allyloxy group), cycloalkyloxy group (e.g. a $C_{3-7}$ cycloalkyloxy group such as cyclopropyloxy group), aralkyloxy group (e.g. a $C_{7-14}$ aralkyloxy group such as benzyloxy group, 1-naphthyloxy group), aryloxy group (e.g. $C_{6-14}$ aryloxy group such as phenyloxy group and naphthyloxy group), mercapto group, a $C_{1-6}$ alkylthio group (e.g. methylthio group, ethylthio group and propiothio group), aralkylthio group (e.g. a $C_{7-15}$ aralkylthio group such as benzylthio group, 1-naphthylthio group,), arylthio group (e.g. a $C_{6-14}$ arylthio group such as phenylthio group and naphthylthio group), sulfo group, cyano group, azido group, nitro group, nitroso group, halogen atom (e.g. fluorine atom, chlorine atom, bromine atom and iodine atom), a $C_{1-3}$ alkylenedioxy group (e.g. methylenedioxy group, ethylenedioxy group) among others.

Said aralkyl group means an alkyl group having an aryl group as substituent (arylalkyl group), and said aryl group is preferably the same as the above-mentioned aryl group, and as a preferable alkyl group, a $C_{1-6}$ alkyl groups is mentioned. A preferable aralkyl group includes, a $C_{7-15}$ aralkyl group, for example, benzyl group, phenethyl group, 3-phenylpropyl group, (1-naphthyl)methyl group and (2-naphthyl)methyl group, especially preferable one being a phenyl-($C_{1-3}$) alkyl group such as benzyl group and phenethyl group.

The aryl group in the aralkyl group may have the same substituents as those which the the above-mentioned aryl group may have, and said substituent is preferably a $C_{1-6}$ alkoxy group (e.g. methoxy group, ethoxy group or propoxy group), a $C_{1-6}$ alkylthio group (e.g. methylthio group, ethylthio group or propylthio group ), especially preferable ones being a $C_{1-3}$ alkoxy group such as methoxy group.

Preferable examples of $R^1$ include hydrogen atom, a $C_{1-6}$ alkyl group (e.g. methyl group, ethyl group), a $C_{7-15}$ aralkyl group optionally substituted by a $C_{1-6}$ alkoxy group or a $C_{1-6}$ alkylthio group (especially preferable one being a phenyl-($C_{1-3}$) alkyl group optionally substituted by a $C_{1-6}$ alkoxy group or a $C_{1-6}$ alkylthio group).

Preferable examples of $R^2$ include hydrogen atom, a $C_{1-6}$ alkyl group (e.g. methyl group, ethyl group, propyl group or isopropyl group).

In the formula (A), $R^3$ means an optionally substituted cyclic hydrocarbon group or an optionally substituted heterocyclic group, and said cyclic hydrocarbon group is exemplified by an aryl group or cycloalkyl group. Said aryl group means the same ones as described referring to $R^1$ and $R^2$, which may have, like the aryl group of $R^1$ and $R^2$, one or more, preferably 1 to 3, appropriate substituents. As said substituent, mention is made of the same ones as described referring to the aryl group of $R^1$ and $R^2$. Especially preferable sustituent includes a $C_{1-6}$ alkyl group, a $C_{3-7}$ cycloalkyl group, a $C_{1-6}$ alkoxy group, cyano group, nitro group, a halogen atom and phenyl group.

Examples of said cycloalkyl group include a $C_{3-10}$ cycloalkyl group or a $C_{3-10}$ bicycloalkyl group, as exemplified by cyclopropyl group, cyclobutyl group, cyclopentyl group, cyclohexyl group, cycloheptyl group, cyclooctyl group, bicyclo[2,2,1]heptyl group, bicyclo[2,2,2]octyl group, bicyclo[3,2,1]octyl group, bicyclo[3,2,1]nonyl group, bicyclo[4,2,1]nonyl group and bicyclo[4,3,1]decyl group. Preferable example of said cycloalkyl group includes a $C_{4-7}$ cycloalkyl group (e.g. cyclobutyl group, cyclopentyl group, cyclohexyl group, cycloheptyl group). Said cycloalkyl group may have 1 to 3, appropriate substituents such as a $C_{1-6}$ alkyl group, a $C_{2-6}$ alkenyl group, a $C_{2-6}$ alkynyl group, carboxyl group, hydroxyl group, nitro group or a halogen atom.

Examples of said heterocyclic group include a 5 to 13-membered aromatic heterocyclic group having, as an atom constituting the ring, 1 to 4 hetero atoms selected from O, S and N, or a saturated or unsaturated non-aromatic heterocyclic group (aliphatic heterocyclic group).

Preferable examples of said heterocyclic group include aromatic monocyclic heterocyclic groups such as furyl group, thienyl group, pyrrolyl group, oxazolyl group, isoxazolyl group, thiazolyl group, isothiazolyl group, imidazolyl group, pyrazolyl group, 1,2,3-oxadiazolyl group, 1,2,4-oxadiazolyl group, 1,3,4-oxadiazolyl group, furazanyl group, 1,2,3-thiadiazolyl group, 1,2,4-thiadiazolyl group, 1,3,4-thiadiazolyl group, 1,2,3-triazolyl group, 1,2,4-triazolyl group, tetrazolyl group, pyridyl group, pyridazinyl group, pyrimidinyl group, pyrazinyl group and triazinyl group; and aromatic condensed heterocyclic groups such as benzofuranyl group, isobenzofuranyl group, benzo[b]thienyl group, indolyl group, isoindolyl group, 1H-indazolyl group, benzoimidazolyl group, benzoxazolyl group, 1,2-benzoisoxazolyl group, benzothiazolyl group, 1,2-benzoisothiazolyl group, 1H-benzotriazolyl group, quinolyl group, quinoline-N-oxide-2-yl group, quinoline-N-oxide-3-yl group, isoquinolyl group, cinnolinyl group, quinazolinyl group, quinoxalinyl group, phthalazinyl group, naphthyridinyl group, purinyl group, pteridinyl group, carbazolyl group, alpha-carbolinyl group, beta-carbolinyl group, gamma-carbolinyl group, acrydinyl group, phenoxazinyl group, phenothiazinyl group, phenazinyl group, phenoxathiinyl group, thianthrenyl group, phenanthridinyl group, phenanthrolinyl group, indolizinyl group, pyrrolo[1,2-b]pyridazinyl group, pyrazolo[1,5-a]pyridyl group, imidazo[1,2-a]pyridyl group, imidazo[1,5-a]pyridyl group, imidazo[1,2-b]pyridazinyl group, imidazo[1,2-a]pyrimidinyl group, 1,2,4-triazolo[4,3-a]pyridyl group and 1,2,4-triazolo[4,3-b]pyridazinyl group. An especially preferable example is pyridyl group, quinolyl group, quinoline-N-oxide-2-yl group, quinoline-N-oxide-3-yl group, benzofuranyl group, benzo[b]thienyl group or thienyl group.

Preferable examples of said non-aromatic heterocyclic group include oxiranyl group, azetidinyl group, oxetanyl group, thietanyl group, pyrrolidinyl group, tetrahydrofuryl group, thiolanyl group, piperidyl group, tetrahydropyranyl group, morpholinyl group, thiomorpholinyl group and piperazinyl group.

And, said heterocyclic group may have one or more, preferably 1 to 3, appropriate substituents, which are the same ones as mentioned referring to the aryl group of $R^1$ and $R^2$. Among them, a $C_{1-6}$ alkyl group is preferable.

Preferable examples of $R^3$ include a $C_{6-14}$ aryl group (e.g. phenyl group, naphthyl group) optionally substituted by at least one selected from the group consisting of $C_{1-6}$ alkyl groups, $C_{3-7}$ cycloalkyl groups, $C_{1-6}$ alkoxy groups, halogen atoms, nitro group, cyano group and phenyl group; or a 5 to 13-membered aromatic heterocyclic group containing 1 to 4 hereto atoms selected from nitrogen atom, oxygen atom and sulfur atom. (e.g. pyridyl group, quinolyl group, quinoline-N-oxide-2-yl group, quinoline-N-oxide-3-yl group, benzofuranyl group, benzo[b]thienyl group, thienyl group) optionally substituted by at least one selected from the group consisting of $C_{1-6}$ alkyl groups, $C_{1-6}$ alkoxy groups, oxo group and hydroxyl group. Among them, phenyl group, naphthyl group, pyridyl group, quinolyl group, thienyl group, quinoline-N-oxide-2-yl group, quinoline-N-oxide-3-yl group, benzofuranyl group, methylbenzo[b]thienyl group and 4-quinolonyl group (e.g. 2-(4-quinolonyl group)) are especially preferable as $R^3$. The 4-quinolonyl group is a quinolyl group substituted by oxo group at 4-position.

In the formula (A), $R^4$ is hydrogen atom, an optionally substituted $C_{1-6}$ alkyl group, an optionally substituted aryl group, an optionally substituted aralkyl group, cyano group, —COOR$^6$ (R$^6$ stands for hydrogen atom, an optionally substituted $C_{1-6}$ alkyl group, an optionally substituted cyclic hydrocarbon group or aralkyl group) or —CONR$^7$R$^7$ (R$^7$, R$^8$ independently stand for hydrogen, an optionally substituted $C_{1-6}$ alkyl group, an optionally substituted cyclic hydrocarbon group or aralkyl group).

Said $C_{1-6}$ alkyl group, aryl group and aralkyl group are the same ones as mentioned referring to $R^1$ and $R^2$, and said cyclic hydrocarbon group means the same ones mentioned referring to $R^3$. Said $C_{1-6}$ alkyl group, aryl group, aralkyl group and cyclic hydrocarbon group may have, like in the cases of $R^1$, $R^2$ and $R^3$, one or more, preferably 1 to 3, appropriate substituents, which are the same ones as described referring to $R^1$, $R^2$ and $R^3$.

Preferable examples of $R^4$ include —COOR$^6$ or —CONR$^7$R$^8$, wherein R$^6$ is preferablly a $C_{1-6}$ alkyl group, a $C_{3-7}$ cycloalkyl group or a $C_{7-15}$ aralkyl group which can optionally be substituted by hydrogen atom, carboxyl group or a 5 to 10-membered heterocyclic group containing 1 to 4 hetero atoms selected from nitrogen atom, oxygen atom and sulfur atom; and R$^7$ and R$^8$ are respectively hydrogen atom, a $C_{1-6}$ alkyl group or a $C_{6-14}$ aryl group. Especially preferable examples of R$^6$ is a $C_{1-6}$ alkyl group substituted by quinolyl group.

Preferable examples of —CONR$^7$R$^8$ include a carbamoyl group or a carbamoyl group substituted by a $C_{1-6}$ alkyl group.

In the formula (A), $R^5$ stands for hydrogen atom, an optionally substituted $C_{1-6}$ alkyl group, an optionally substituted aryl group, an optionally substituted aralkyl group or —$X^1R^9$ ($X^1$ stands for —O—, —$NR^{10}$— or —S—; $R^9$ and $R^{10}$ independently stand for hydrogen atom, an optionally substituted $C_{1-6}$ alkyl group, an optionally substituted aryl group or an optionally substituted aralkyl group). The $C_{1-6}$ alkyl group, aryl group and aralkyl group in $R^5$, $R^9$ and $R^{10}$ are the same ones as mentioned referring to $R^1$ and $R^2$, and said aryl group and aralkyl group may have, like in the cases of $R^1$, $R^2$ and $R^3$, one or more, preferably 1 to 3, appropriate substituents. As those substituents, mention is made of the same ones as described referring to $R^1$ and $R^2$.

Preferable examples of $R^5$ include hydrogen atom, an optionally substituted $C_{1-6}$ alkyl group, an optionally substituted aryl group, especially preferable ones being hydrogen atom, a $C_{1-6}$ alkyl group (e.g. methyl group, ethyl group, propyl group, isopropyl group and isobutyl group) or a $C_{6-14}$ aryl group (e.g. phenyl group) optionally substituted by $C_{1-3}$ alkylenedioxy group.

Preferable examples of the compound [A] of this invention include the compound wherein n denotes an integer of 1 to 3; $R^1$ is hydrogen atom, a $C_{1-6}$ alkyl group, or a $C_{7-15}$ aralkyl group optionally substituted by a $C_{1-6}$ alkoxy group or $C_{1-6}$ alkylthio group; $R^2$ is hydrogen atom or a $C_{1-6}$ alkyl group; $QR^3$ is a $C_{6-14}$ aryl group optionally substituted by at least one selected from the group consisting of $C_{1-6}$ alkyl groups, $C_{3-7}$ cycloalkyl groups, $C_{1-6}$ alkoxy groups, halogen atoms, nitro group, cyano group and phenyl group; or a 5 to 13-membered aromatic heterocyclic group containing 1 to 4 hetero atoms selected from nitrogen atom, oxygen atom and sulfur atom optionally substituted by at least one selected from the group consisting of $C_{1-6}$ alkyl groups, $C_{1-6}$ alkoxy groups, oxo group and hydroxyl group; $R^4$ is —$COOR^{61}$ ($R^{61}$ is hydrogen atom, a alkyl group optionally substituted by carboxyl group or a 5 to 10-membered heterocyclic group containing 1 to 4 hetero atoms selected from nitrogen atom, oxygen atom and sulfur atom; $C_{3-7}$ cycloalkyl group; or 6–15 aralkyl group) or —$CONR^{71}R^{81}$ ($R^{71}$ and $R^{81}$ independently are hydrogen atom, $C_{1-6}$ alkyl group, or $C_{6-14}$ aryl group); $R^5$ is hydrogen atom, a $C_{1-6}$ alkyl group, or a $C_{6-14}$ aryl group optionally substituted by a $C_{1-3}$ alkylenedioxy group. An especially preferable example is the one wherein the 5 to 13-membered aromatic heterocyclic group containing 1 to 4 hetero atoms selected from nitrogen atom, oxygen atom and sulfur atom of $R^3$ is selected from the group consisting of pyridyl group, quinolyl group, quinoline-N-oxide-2-yl group, quinoline-N-oxide-3-yl group, benzofuranyl group, benzo[b]thienyl group and thienyl group; and the 5 to 10-membered heterocyclic group containing 1 to 4 hetero atoms selected from nitrogen atom, oxygen atom and sulfur atom of $R^{61}$ is quinolyl group.

The specific examples of preferable compound of this invention, include 2,4(1H,3H)-dioxo-6-ethoxycarbonyl-7-isopropyl-1-(2-methoxybenzyl)-5-(4-tolyl)pyrido[2,3-d]pyrimidin-3-acetic acid, 2,4(1H,3H)-dioxo-6-ethoxycarbonyl-7-methyl-1-(2-methoxybenzyl)-5-(4-methoxyphenyl)pyrido[2,3-d]pyrimidine-3-acetic acid, ethyl[2,4(1H,3H)-dioxo-6-carboxy-7-isopropyl-1-(2-methoxybenzyl)-5-[2-(4-quinolonyl)]pyrido[2,3-d]pyrimidine]-3-acetate, 2,4(1H,3H)-dioxo-6-carboxy-7-isopropyl-1-(2-methoxybenzyl)-5-[2-(4-quinolonyl)]pyrido[2,3-d]pyrimidine-3-acetic acid, 2,4(1H,3H)-dioxo-6-carboxy-7-isopropyl-1-(2-methylthiobenzyl)-5-[2-(4-quinolonyl)]pyrido[2,3-d]pyrimidine-3-acetic acid and their salts.

As salts of the compound [A] of this invention, pharmaceutically acceptable acid addition salts are mentioned as especially preferable ones. As such salts, use is made of, for example, those with an inorganic acid (e.g. hydrochloric acid, phosphoric acid, hydrobromic acid or sulfuric acid) or those with an organic acid (e.g. acetic acid, formic acid, propionic acid, fumaric acid, maleic acid, succinic acid, tartaric acid, citric acid, malic acid, oxalic acid, benzoic acid, methanesulfonic acid or benzenesulfonic acid). And, in the case where the compound [A] of this invention has an acid group such as —COOH, the compound [A] may form a salt with an inorganic base (e.g. an alkali metal or alkaline earth metal such as sodium, potassium, calcium or magnesium; or ammonia) or an organic base (e.g. trialkylamine having a $C_{1-8}$ alkyl groups, such as triethylamine).

As salts of the starting compounds for producing the compound [A] of this invention, use is made of, for example, salts with an inorganic acid (e.g. hydrochloric acid, phosphoric acid, hydrobromic acid or sulfuric acid) or salts with an organic acid (e.g. (acetic acid, formic acid, propionic acid, fumaric acid, maleic acid, succinic acid, tartaric acid, citric acid, malic acid, oxalic acid, benzoic acid, methanesulfonic acid or benzenesulfonic acid). And, in the case where the starting compound has an acid group such as —COOH, it may form a salt with an inorganic base (e.g. an alkali metal or alkaline earth metal such as sodium potassium, calcium or magnesium; or ammonia) or an organic base (e.g. trialkylamine having a $C_{1-8}$ alkyl group, such as triethylamine).

The compound [A] of this invention and salts thereof can be readily produced by per se known methods, and, as typical ones, the following seven methods are mentioned.

[Production Method—1]

A urea derivative (i) represented by the formula $R^{1'}NHCONH_2$ ($R^{1'}$ stands for an optionally substituted $C_{1-6}$ alkyl group, aryl group or aralkyl group), which is synthesized from a $C_{1-6}$ alkylamine, arylamine or aralkylamine is heated in an appropriate solvent such as ethyl alcohol in the presence of a cyanoacetic acid derivative and a base, at the temperature of 80°–120° C. for 2–240 hours, preferablly 24–100 hours, to give a 1-($C_{1-6}$ alkyl)substituted, 1-aryl-substituted or 1-aralkyl-substituted 6-aminopyrimidine-2,4 (1H,3H)-dione derivative (ii).

This compound is stirred, together with a halogenated acetic acid ester derivative or a halogenated propionic acid ester derivative, in the presence of a base in an appropriate solvent such as dimethylacetamide or dimethylformamide at the temperature of 40°–70° C., usually for 4–96 hours, preferablly 12–24 hours, to give a 6-amino-2,4(1H,3H)-dioxopyrimidine-3-acetic acid ester derivative or a 6-amino-2,4(1H,3H)-dioxopyrimidine-3-propionic acid ester derivative represented by the formula (I').

The derivative (I') thus obtained is, in accordance with the Hantzsch's synthetic method [A. Hantzsch, Ann. Chem. 215, 1 (1882)], subjected to heating with arylaldehyde and beta-keto ester under reflux at the temperature of 80°–100° C., usually for 2–240 hours, preferablly 12–120 hours, in an appropriate solvent such as ethyl alcohol, or subjected beforehand to Knoevenagel condensation reaction [T. Yamamori, Y. Hiramatsu, K. Sakai and I. Adachi, Tetrahedron, 41, 913 (1985)] to synthesize a dehydrated condensed derivative with arylaldehyde and beta keto ester, then the dehydrated condensed derivative and the derivative (I') are heated under reflux at the temperature of 100°–130° C., usually for 2–240 hours, preferablly 12–120 hours, in an appropriate solvent such as toluene to give 5,8- dihydropyrido[2,3-d]pyrimidine-2,4-dione derivative (B1). This compound (B1) is subjected to oxidation with an appropriate oxidizing agent such as sodium nitrite in acetic acid to give the compound (A1) of this invention. Further, if necessary, the compound (A1) is subjected to an appropriate conditions, for example, alkali hydrolysis in an appropriate solvent such as methanol, ethanole, tetrahydrofuran or dioxane to give the compound (A2) of this invention. The alkali hydrolysis reaction can be carried out by stirring the reaction mixture in the presence of an appropriate base catalyst (e.g. sodium hydroxide, litium hydroxide, potassium hydroxide and others), at room temperature or at the elevated temperature (e.g. 40°–100° C.), usually for 2–48 hours, preferablly 2–24 hours.

The reactions in the above-described production method are collectively shown by the following reaction scheme, in which each symbol is of the same meaning as defined above.

Production Method-1

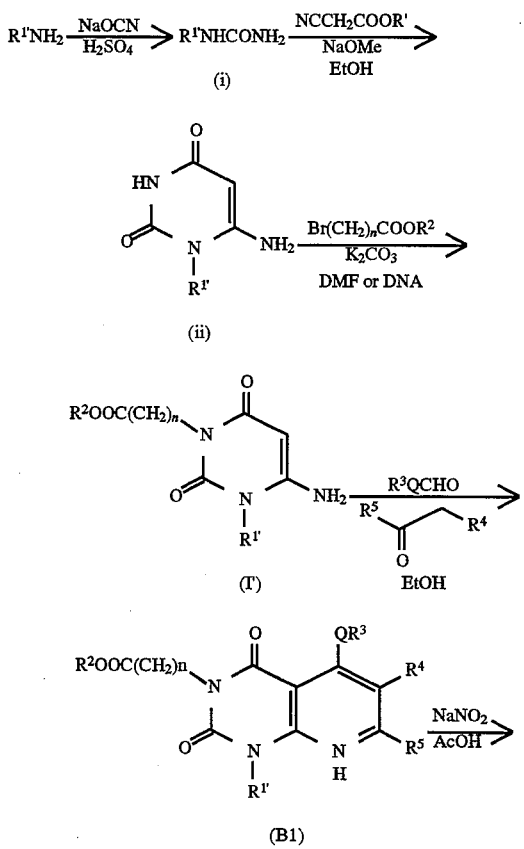

-continued
Production Method-1

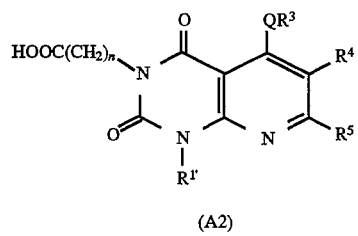

[Production Method—2]

In accordance with an analogous method to that reported by Y. Tominaga et al. [Chim. Pharm. Bull., 32, 122 (1984)], 6-amino-2,4(1H,3H)-dioxopyrimidine-3-acetic-acid ester derivative (I') is heated with a 3,3-bismethylthio derivative in dimethylformamide, at the temperature of 100°–150° C., usually for 1–12 hours, preferablly 2–6 hours, to give a pyrido[2,3-d]pyrimidine-2,4-dione derivative (C1). A nucleophilic reagent represented by the formula $R^3QH$ ($R^3$ and Q are of the same meaning as defined above) is allowed to react with the compound (C1), at the temperature of 40°–100° C., usually for 2–120 hours, preferablly 2–24 hours, in an appropriate solvent (e.g. methanol, ethanol, tetrahydrofuran, dioxane or dimethylformamide), to give the compound (A1) of this invention.

Further, if necessary, the compound (A1) is subjected to an appropriate conditions, for example, alkali hydrolysis in an appropriate solvent such as methanol, ethanol, tetrahydrofuran or dioxane to give the compound (A2) of this invention. The alkali hydrolysis reaction can be carried out by stirring the reaction mixture in the presence of an appropriate base catalyst (e.g. sodium hydroxide, litium hydroxide, potassium hydroxide and others), at room temperature or at the elevated temperature (e.g. 40°–100° C.), usually for 2–48 hours, preferablly 2–24 hours. The above reactions are collectively shown in the following reaction scheme, in which $R^{1'}$ is an optionally substituted $C_{1-6}$ alkyl group, aryl group or aralkyl group and each symbol except $R^{1'}$ is of the same meaning as defined above. (0029)

[Production Method—2]

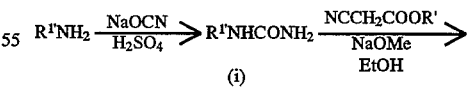

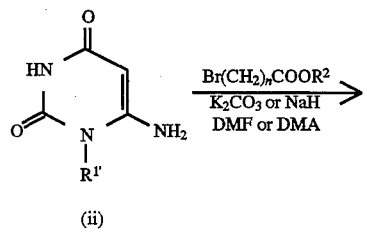

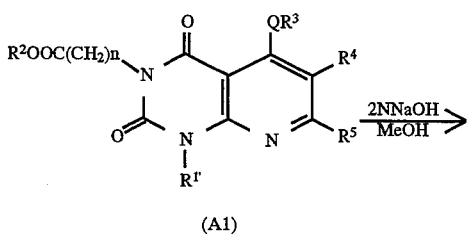

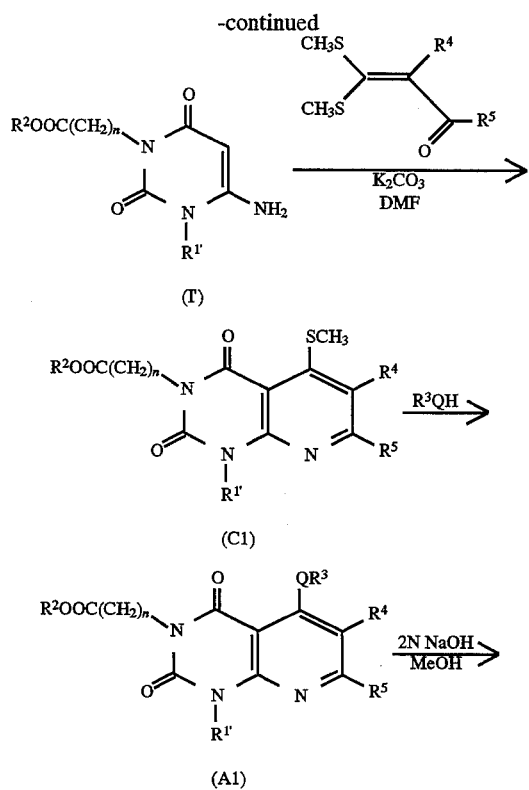

presence of a base (e.g. sodiumu hydride, potassium carbonate), in an appropreate solvent (e.g. dimethylacetamide, dimethylformamide), at room temperature or at an elevated temperature such as 40°–120° C., for usually 0.5–12 hours, preferably 0.5–2 hours to give the compound (A1), 3-position acetic acid ester or propionic acid ester derivative, of this invention.

Further, if necessary, the compound (A1) is subjected to alkali hydrolyzing in an appropriate solvent such as methanol, ethanol, tetrahydrofuran or dioxane to give the compound (A2) of this invention. The alkali hydrolysis reaction can be carried out by stirring the reaction mixture in the presence of an appropriate base catalyst (e.g. sodium hydroxide, litium hydroxide, potassium hydroxide and others), at room temperature or at an elevated temperature (e.g. 40°–100° C.), usually for 2–12 hours.

The reactions in the above-described production method are collectively shown by the following reaction scheme, in which each symbol is of the same meaning as defined above.

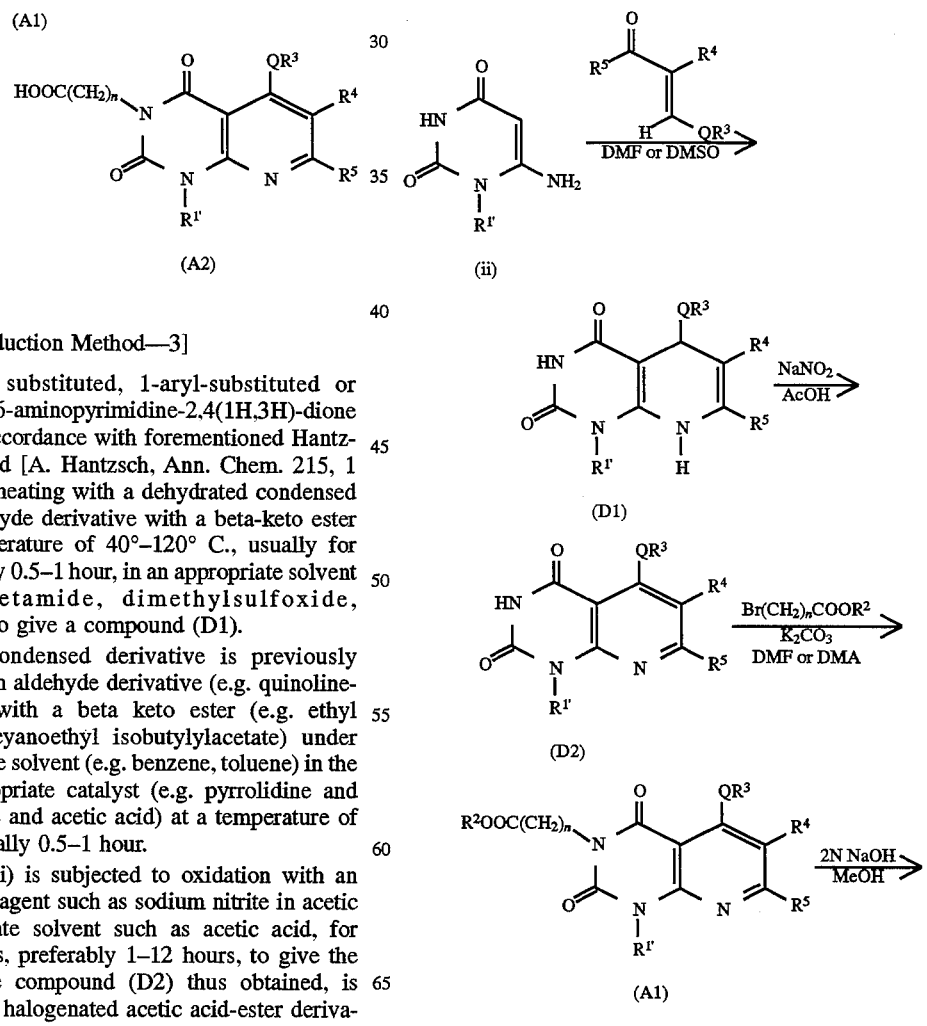

[Production Method—3]

A 1-($C_{1-6}$ alkyl) substituted, 1-aryl-substituted or 1-aralkyl-substituted 6-aminopyrimidine-2,4(1H,3H)-dione derivative (ii) is, in accordance with forementioned Hantzsch's synthetic method [A. Hantzsch, Ann. Chem. 215, 1 (1882)], subjected to heating with a dehydrated condensed derivative of an aldehyde derivative with a beta-keto ester derivative, at a temperature of 40°–120° C., usually for 0.5–4 hours, preferably 0.5–1 hour, in an appropriate solvent (e.g. dimethylacetamide, dimethylsulfoxide, dimethylformamide) to give a compound (D1).

The dehydrated condensed derivative is previously obtained by heating an aldehyde derivative (e.g. quinoline-2-carboxyaldehyde) with a beta keto ester (e.g. ethyl isobutylylacetate, 2-cyanoethyl isobutylylacetate) under reflux in an appropriate solvent (e.g. benzene, toluene) in the presence of an appropriate catalyst (e.g. pyrrolidine and acetic acid, piperidine and acetic acid) at a temperature of 100°–120° C. for usually 0.5–1 hour.

This compound (Di) is subjected to oxidation with an appropriate oxidizing agent such as sodium nitrite in acetic acid, in an appropriate solvent such as acetic acid, for usually 0.25–24 hours, preferably 1–12 hours, to give the compound (D2). The compound (D2) thus obtained, is allowed to stir with a halogenated acetic acid-ester derivative or a halogenated propionic acid-ester derivative, in the

19

-continued
Production Method-3

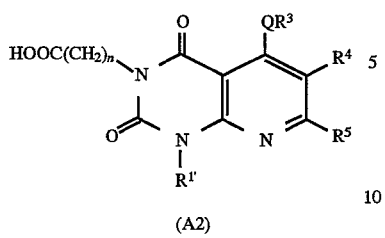

(A2)

[Production Method—4]

Here is an example of changing the substituent in the compound of this invention.

A 5-(2-quinolyl)-6-cyanoethoxycarbonyl derivative (E1) is subjected to stirring in an appropriate solvent (e.g. methanol, ethanol, tetrahydrofuran or dioxane) in the presence of an appropriate weak base (e.g. aqueous solution of sodium carbonate or sodium hydrogen carbonate), at room temperature or at an elevated temperature (e.g. 40°–100° C.), usually for 2–12 hours, preferably 0.5–2 hours to give a 6-carboxyl derivative (E2).

The compound (E2) is dissolved in an appropriate solvent (e.g. methylene chloride, carbon tetrachloride, 1,2-dichloroethane or toluene) and subjected to heating and reacting with much excess of thionyl chloride (e.g. 10 times of equivalent) under reflux (e.g. 40°–120° C.) for usually 5–120 minutes, preferably 5–60 minutes. The reaction mixture was then concentrated to dryness while removing the excess of thionyl chloride. The residue is dissolved in an appropriate solvent (e.g. acetonitrile, tetrahydrofuran, dioxane or dimethylacetamide). Being added an appropreate weak base (e.g. aqueous solution of sodium carbonate or sodium hydrogen carbonate), the solution is subjected to stirring at room temperature or at an elevated temperature (e.g. 40°–100° C.), usually for 2–48 hours, preferably 2–24 hours to give 4-quinolonyl derivative (A3).

Further, if necessary, the compound (A3) is subjected to alkali hydrolyzing in an appropriate solvent such as methanol, ethanol, tetrahydrofuran or dioxane to give the compound (A4) of this invention. The alkali hydrolysis reaction can be carried out by stirring the reaction mixture in the presence of an appropriate base catalyst (e.g. sodium hydroxide, litium hydroxide, potassium hydroxide and others), at room temperature or at an elevated temperature (e.g. 40°–100° C.), usually for 2–12 hours.

The reactions in the above-described production method are collectively shown by the following reaction scheme, in which $R^{2'}$ is an optionally substituted $C_{1-6}$ alkyl group, aryl group or aralkyl group and each symbol except $R^{2'}$ is of the same meaning as defined above.

20

[Production Method-4]

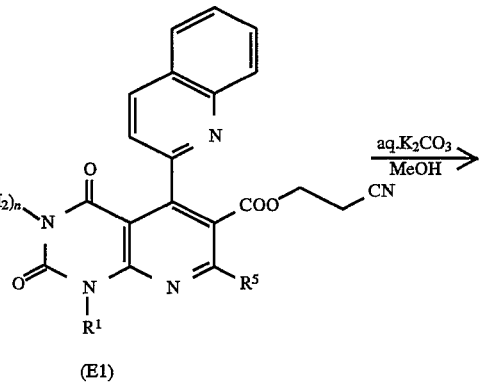

(E1)

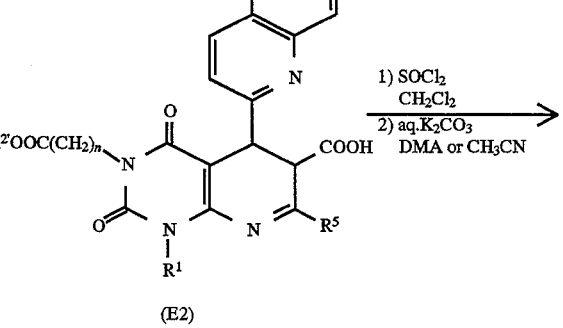

(E2)

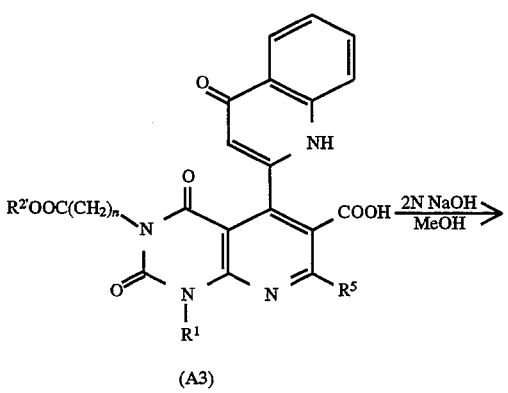

(A3)

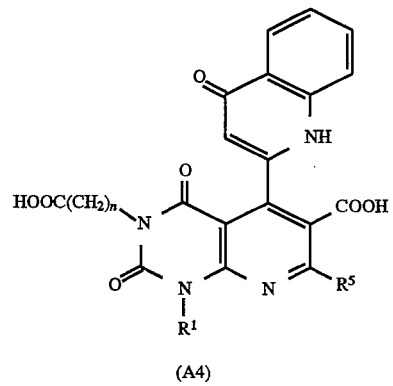

(A4)

[Production Method—5]

A 1-(2,4-dimethoxybenzyl) derivative (F1) is subjected to oxidizing to give 1-hydro derivative (F). The oxidization is carried out as follows.

The compound (F1) is dissolved in an appropriate solvent (e.g. an aqueous solution of acetone or acetonitrile), to which an appropriate oxidizing agent such as cerium ammonium nitrate (CAN) is added, and the mixture is allowed to stir at room temperature or at an elevated temperature (e.g. 40°–60° C.), usually for 0.5–2 hours, preferably 0.5–1 hour to give the compound (F).

Another method of oxidization comprises stirring the compound (F1) in trifluoroacetic acid (TFA) at a temperature of 40°–80° C., usually for 1–12 hours, preferably 2–6 hours to give the compound (F). The compound (F) thus obtained is subjected to reacting by stirring with a halogenated lower alkyl derivative (e.g. methyl iodide) or a halogenated aralkyl derivative (e.g. substituted benzyl chloride derivative or substituted benzyl bromide derivative) in an appropriate solvent (e.g. dimethylacetamide, dimethylformamide, acetone or tetrahydrofuran) in the presence of an appropriate base (e.g. sodium hydride or potassium carbonate), usually for 0.5–4 hours, preferably 0.5–2 hours to give the compound (A).

Further, if necessary, the compound (A) is subjected to alkali hydrolyzing in an appropriate solvent such as methanol, ethanol, tetrahydrofuran or dioxane to give the compound (Aa) of this invention. The alkali hydrolysis reaction can be carried out by stirring the reaction mixture in the presence of an appropriate base catalyst (e.g. sodium hydroxide, litium hydroxide, potassium hydroxide and others), at room temperature or at an elevated temperature (e.g. 40°–100° C.).

The reactions in the above-described production method are collectively shown by the following reaction scheme, in which each symbol is of the same meaning as defined above.

[Production Method—5]

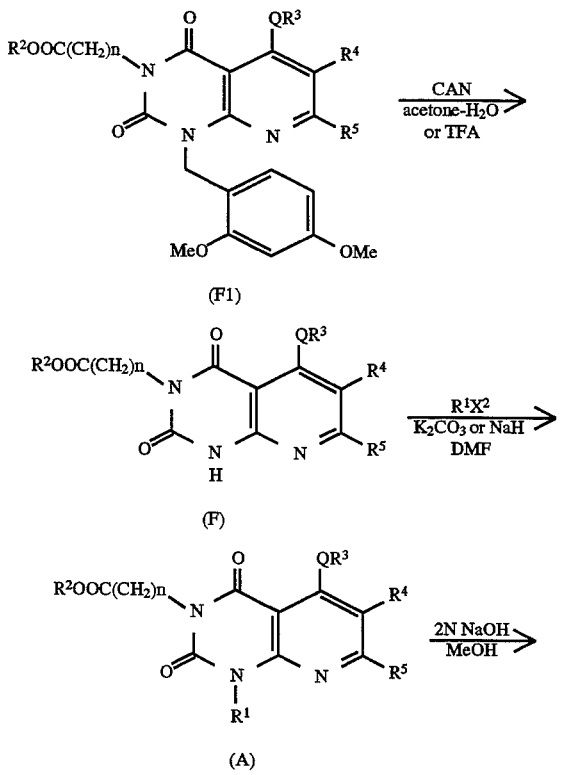

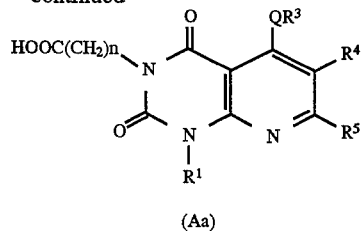

CAN:Cerium(IV)ammonium nitrate
TFA:Trifluoroacetic acid

[Production Method—6]

Here is an example of the process for producing the compound (A) of this invention wherein the substituent at 6-position is —COOR⁶' (R⁶' is an optionally substituted $C_{1-6}$ alkyl group, an optionally substituted cyclic hydrocarbon group or an optionally substituted aralkyl group).

The compound (A9), whose substituent at 6-position is COOH, is subjected to stirring with a halogenated alkyl, a halogenated cyclic hydrocarbon or halogenated aralkyl derivative (e.g. ethyl bromide, isobutyl bromide or benzyl bromide) in an appropriate solvent (e.g. dimethylacetamide or dimethylformamide) in the presence of an appropriate weak base (e.g. potassium carbonate, triethylamine or sodium hydrogen carbonate), usually for 2–48 hours, preferably 2–24 hours to give a compound (A10) of this invention whose substituent at 6-position is —COOR⁶'.

Further, if necessary, the compound (A10) is subjected to alkali hydrolyzing in an appropriate solvent such as methanol, ethanol, tetrahydrofuran or dioxane, or acid hydrolyzing in an appropriate solvent such as methylene chloride to give the compound (A11) of this invention.

The alkali hydrolysis reaction can be carried out by stirring the reaction mixture in the presence of an appropriate base catalyst (e.g. sodium hydroxide, litium hydroxide, potassium hydroxide and others), at room temperature or at an elevated temperature (e.g. 40°–100° C.), usually for 2–48 hours, preferably 2–24 hours.

The acid hydrolysis reaction can be carried out by stirring the reaction mixture with a catalytic amount or excessive amount of an appropriate acid such as trifluoroacetic acid, at room temperature or at an elevated temperature (e.g. 40°–100° C.), usually for 2–48 hours, preferably 2–24 hours.

The reactions in the above-described production method are collectively shown by the following reaction scheme, in which each symbol is of the same meaning as defined above.

Production Method - 6

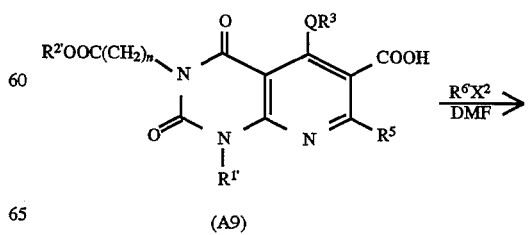

-continued

Production Method - 6

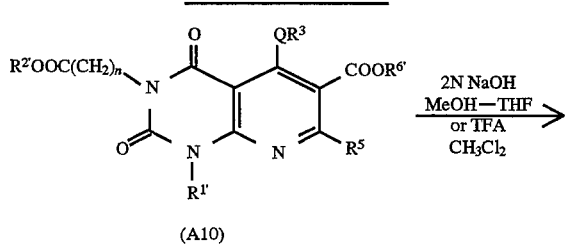
(A10)

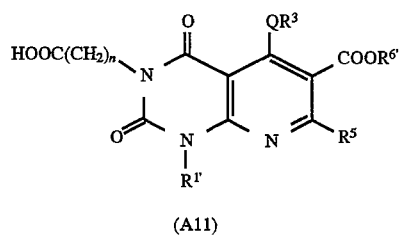
(A11)

[Production Method—7]

Here is an example of the process for producing the compound (A) of this invention wherein the substituent at 5-position is 2-(4-quinolonyl) group and at 6-position is —COOR$^6$ or —CONR$^7$R$^8$ (R$^6$, R$^7$ and R$^8$ are independently hydrogen atom, an optionally substituted C$_{1-6}$ alkyl group, an optionally substituted aralkyl group).

The compound (A12), whose substituent at 1-position is hydrogen atom, is subjected to stirring with excess of thionyl chloride (e.g. 5–20, preferably 5–10 times of equivalent) in an appropriate solvent (e.g. methylene chloride or toluene) at room temperature or at an elevated temperature (e.g. 40°–60° C.), usually for 0.5–2 hours, preferably 0.5–1 hour. The reaction mixture is then concentrated to dryness under reduced pressure. The residue is dissolved in an appropriate solvent (e.g. methylene chloride). Filtered off the insoluble material (e.g. by filtration with sellaite), the filtrate is concentrated to dryness, and if necessary washed with an appropriate solvent (e.g. ethyl acetate), to give the compound (H1).

The compound (H1) thus obtained is dissolved in an appropriate solvent (e.g. dimethylformamide, dimethylacetamide or acetonitrile), and then is subjected to stirring with usually 1–3, preferably 1–1.5 times of equivalent of an appropriate halogenated alkyl derivative or halogenated aralkyl derivative (e.g. 2-methylthiobenzyl chloride or 2,3-dimethoxybenzyl chroride etc.) in the presence of usually 1–3, preferably 1.5–2 times of equivalent of an appropriate base (e.g. potassium hydrogencabonate, pottasium carbonate or sodium hydride ), at room temperature or at an elevated temperature (e.g. usually 40°–100° C., preferably 40°–60° C.) usually for 2–48 hours, preferably 24–48 hours to give the compound (H2).

After refining by appropriate method (e.g. silica gel column chromatography), if necessary the compound (H2) is dissolved in an appropriate solvent (e.g. acetonitrile or dimethylacetamide), and then is subjected to stirring with excess (usually 5–30, preferably 5–10 times of equivalent) of a nucleophilic reagent (e.g. 2N aqueous solution of pottasium carbonate, aqueous ammonia or an amine compound) at room temperature or at an elevated temperature (e.g. usually 40°–120° C., preferably 40°–80° C.) usually for 1–6 hours, preferably 1–2 hours to give the compound (A13). The reactions in the above-described production method are collectively shown by the following reaction scheme, in which R is —OR$^6$ or —NR$^7$R$^8$ and each symbol except R is of the same meaning as defined above.

Production Method - 7

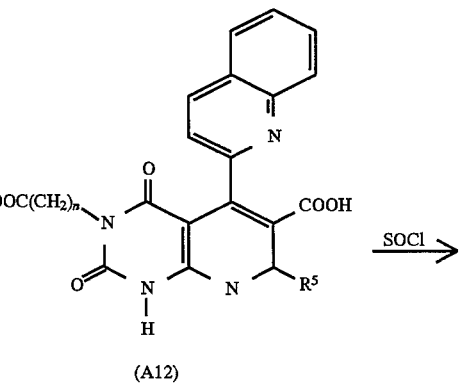
(A12)

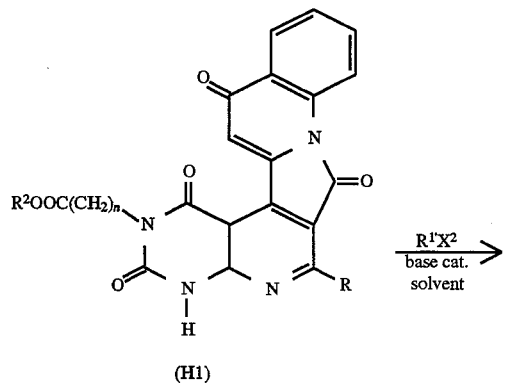
(H1)

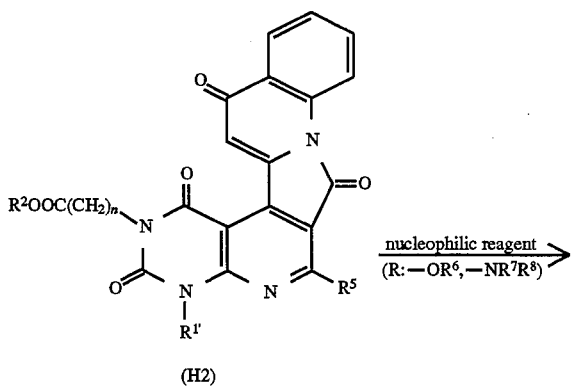
(H2)

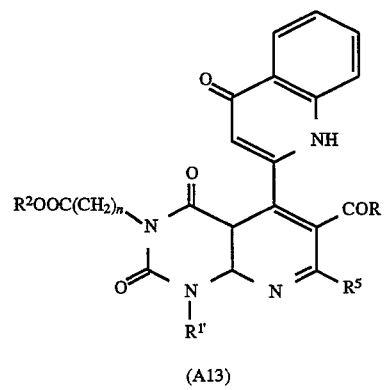
(A13)

In the above-described [Production Method—1] and [Production Method—2], the compound [A] wherein R$^1$=H can be produced by, using a compound represented by $R^{1'''}NH_2$ ($R^{1'''}$ stands for a protective group of ammonia) instead of the starting compound $R^1NH_2$ ($R^{1'}$ is of the same meaning as defined above), then removing the protecting group shown by $R^{1'''}$ adequately during or after the reaction.

In the above-described [Production Method—3], the compound [A] wherein $R^1$=H can be produced by, using a compound (ii) having $R^{1'}$ ($R^{1'}$ stands for a protective group of ammonia) instead of $R^{1'}$ ($R^{1'}$ is of the same meaning as defined above), then removing the protecting group shown by $R^{1'''}$ adequately during or after the reaction.

The compound $R^{1'''}NH_2$ can be produced by a per se known method or an analogous method thereto, or is commercially available.

For removing the protective group, a per se known method or a method analogous thereto can be employed, for example, by the use of an acid, a base, an oxidizing agent, a reducing agent, ultraviolet ray, hydrazine, phenyl hydrazine, sodium N-methyldithiocarbamate, tetrabutylammonium fluoride, palladium acetate, etc.

The starting compounds, $C_{1-6}$ alkylamine, arylamine and aralkylamine can be produced by a per se known method or an analogous method thereto.

The compound [A] thus obtained or a salt thereof can be isolated and purified in conventional manner, e.g. by recrystallization, distillation or chromatography. When the compound [A] is thus obtained as a free compound, it can be converted to a corresponding salt by a per se known method or an analogous method thereto, and, when the compound [A] is obtained as a salt, it can be converted to a free compound or any other salt by a per se conventional method or an analogous method thereto.

In the case where the compound [A] or a salt thereof is an optically active compound, it can be isolated into d-isomer and l-isomer by a conventional means for optical resolution.

The compound [A] or its salt of this invention has excellent endothelin receptor antagonistic activity, therefore, it can be used as endothelin receptor antagonist for warm-blooded animals (e.g. rat, mouse, guinea pig, chicken, dog, cat, sheep, pig, bovine, monkey, man and others).

Moreover, because of its excellent endothelin receptor antagonistic activity, the compound [A] or its salt of this invention can be used as prophylactic and therapeutic composition against cerebral infarction, angina pectoris, myocardial infarction and renal insufficiency.

The compound [A] or its salt of this invention is of a salty and low toxycity.

When the compound [A] or its salt of this invention is used as endothelin receptor antagonist or as prophylactic and therapeutic agents against acute renal insufficiency, myocardial infarction, hypertension, cerebral infarction, angina pectoris, arteriosclerosis, hepatopathy, pulmonary hypertension, bronchial asthma, organohypofunction occuring during operation or transplantation of organs.

They can be administered either orally or non-orally. Usually, they are administered orally in a form of a solid preparation such as tablets, capsules, granules or powder, or non-orally in a form of intravenous, subcutaneous or intramuscular injection, suppositories or sublingual tablets. Dosage amounts will vary with degrees of symptoms; ages of patients, sex, body weight, difference in sensitivity; administration time; interval, quality of medicinal preparations, preparation, kinds; kinds of effective components, among others, and they are not specifically limited. Usually, the dosage for adult per day ranges from about 0.1 to 500 mg, preferably from about 1 to 100 mg, more preferably from 5 to 50 mg, in one to 4 divided doses per day.

The compounds of this invention can be administered orally or non-orally, formulated with pharmaceutically acceptable carriers, as a solid preparation including tablets, capsules, granules and powder, or as a liquid preparation such as syrup or injections.

The above-mentioned pharmaceutically acceptable carriers include conventional organic or inorganic carriers employed in the field of pharmaceutical preparations; namely, excipients, lubricants, binders and disintegrators in solid preparations; solvents, solubilizers, suspending agents, isotonizers, buffer agents and local anesthetics in liquid preparations. Upon necessity, additives such as preservatives, antioxidants, colorants, sweeteners or the like can also be employed.

Preferable excipients are exemplified by lactose, sucrose, D-mannitol, starch, crystalline cellulose and light silicic acid anhydride.

Preferable lubricants are exemplified by magnesium stearate, calcium stearate, talc and colloidal silica.

Preferable binders are exemplified by crystalline cellulose, sucrose, D-mannitol, dextrin, hydroxypropyl cellulose, hydroxypropyl methyl cellulose and polyvinyl pyrrolidone.

Preferable disintegrators are exemplified by starch, carboxymethyl cellulose, carboxymethyl cellulose calcium, closcarmellose sodium and carboxymethyl starch sodium.

Preferable solvents are exemplified by distilled water for injection, alcohol, propylene glycol, macrogol, sesame oil and corn oil.

Preferable solubilizers are exemplified by polyethylene glycol, propylene glycol, D-mannitol, benzyl benzoate, ethanol, trisaminomethane, cholesterol, triethanolamine, sodium carbonate and sodium citrate.

Preferable examples of suspending agents include surfactants such as stearyl triethanolamine, sodium lauryl sulfate, laurylaminopropionic acid, lecithin, benzalkonium chloride, benzethonium chloride and glycerin monostearate; hydrophilic polymers such as polyvinyl alcohol, polyvinyl pyrrolidone, carboxymethyl cellulose sodium, methyl cellulose, hydroxymethyl cellulose, hydroxyethyl cellulose and hydroxypropyl cellulose.

Preferable isotonizers are exemplified by sodium chloride, glycerin and D-mannitol.

Preferable buffer agents are exemplified by buffer solutions such as phosphates, acetates, carbonates and citrates.

Preferable local anesthetics are exemplified by benzyl alcohol.

Preferable preservatives are exemplified by para-hydroxybenzoic esters, chlorobutanol, benzyl alcohol, phenethyl alcohol, dehydroacetic acid and sorbic acid.

Preferable antioxidants are exemplified by sulfite and ascorbic acid.

By the addition of a suspending composition, a solubilizer, a stabilizing composition, an isotonizer, a preservative or the like to the compound of this invention, intravenous, subcutaneous and intramuscular injections are prepared by conventional methods. Upon necessity, these injections can be made into lyophilized preparations.

EXAMPLES

The following examples are given for the purpose of illustration and not by any of limitation.

Reference Example 1

Production of 2-methoxybenzyl Urea
(Chemical Formula 1)

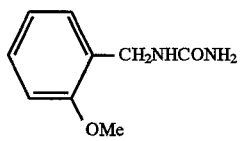

To an aqueous solution (13 ml) containing 2-methoxybenzylamine (13.7 g, 0.1 mol.) was added dropwise dilute sulfuric acid (prepared from 2.8 ml of conc. sulfuric acid and 6.7 ml of refined water) at room temperature. After completion of the dropwise addition, an aqueous solution (70 ml) containing sodium cyanate (7.65 g, 0.12 mol.) was added to the reaction mixture at room temperature taking 15 minutes. The suspension obtained as reaction mixture was heated at 80° C. for one hour. The reaction mixture was cooled, then resulting crystalline precipitates were collected by filtration, followed by recrystallization from ethanol to give 17 g (yield 94%) of colorless prisms.

Reference Example 2

Production of 6-amino-1-(2-methoxybenzyl) pyrimidine-2,4 (1H,3H)-dione
(Chemical Formula 2)

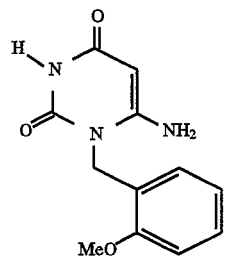

A mixture of the compound (10.8 g, 60 mmol.) obtained in Reference Example 1, ethyl cyanoacetate (7.0 g, 62 mmol.) and sodium methoxide (28% methanol solution, 12.0 g, 62 mmol.) was heated for 72 hours in ethanol (100 ml) under reflux. The reaction mixture was cooled, which was then concentrated to dryness. To the concentrate was added a saturated aqueous solution of ammonium chloride (50 ml). The mixture was stirred, then the pH thereof was adjusted to a range of 6 to 7 with 1N HCl.

Resulting precipitates were collected by filtration and recrystallized from a mixture of ethanol and methanol (1:1) to give 10.0 g (yield 68%) of pale yellow prisms, m.p. 278° to 279° C. The elemental analysis values were as shown in Table 1.

TABLE 1

| Elemental Analysis for $C_{12}H_{13}N_3O_3$ | | | |
|---|---|---|---|
| | C (%) | H (%) | N (%) |
| Calcd. | 58.29 | 5.30 | 16.99 |
| Found | 58.00 | 5.36 | 17.01 |

Reference Example 3

The method described as Reference Example 1 and 2 was repeated, while employing various substituted amino compounds in place of 2-methoxybenzylamine. The compounds represented by chemical formula (3) thus obtained were collectively shown in the following Table 2.

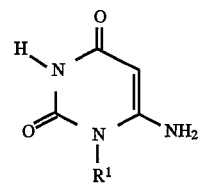

TABLE 2

| Ref. Ex. 3 Cpd. No. | 1-substituent ($R^1$) | m.p. (°C.) |
|---|---|---|
| 1 | 2,4-dimethoxybenzyl | powder(X) |
| 2 | 3-methoxybenzyl | 290–294 |
| 3 | 3,4-methylenedioxybenzyl | 290–298 |
| 4 | 2-methoxyphenyl | 288–290 |

(X) powder:non-crystalline powder (the same in the following table)

Reference Example 4

Production of Ethyl [6-amino-2,4(1H,3H)-dioxo-1-(2-methoxybenzyl)]pyrimidine-3-acetate
(Chemical Formula 4)

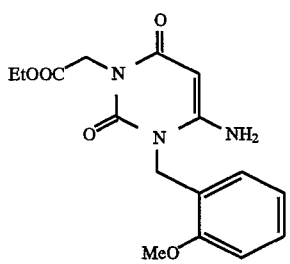

A mixture of the compound (6.65 g, 27 mmol.) obtained in Reference Example 2, ethyl bromoacetate (15.0 g, 90 mmol.) and potassium carbonate (16.6 g, 120 mmol.) was stirred in dimethylformamide (500 ml) for 72 hours at 60° C. The reaction mixture was, after cooling, concentrated to dryness, to which were added a saturated aqueous solution of ammonium chloride (30 ml) and ethyl acetate (50 ml), then the mixture was stirred. The organic layer was separated. The aqueous layer was subjected to extraction with ethyl acetate (50 ml). The extract was combined with the organic layer, which was then dried. The solvent was distilled off under reduced pressure. The residue was purified by means of a silica gel column chromatography to give 3.5 g (yield 39%) of a yellow amorphous product.

The NMR spectrum of thus obtained yellow amorphous compound was as follows.

$^1$H-NMR (200 MHz, $CDCl_3$) δ ppm: 1.27(3H, t), 3.93 (3H,s), 4.21(2H,q), 4.70(2H,s), 4.91(1H,s), 5.12(2H,s), 5.31 (2H,s), 6.91–7.03(2H,m), 7.27–7.40(1H,m), 7.50–7.55(1H, m).

Reference Example 5

Production of Ethyl [5,8-dihydro-2,4(1H,3H)-dioxo-6-ethoxycarbonyl-7-isopropyl-1-(2-methoxybenzyl)-5-(4-tolyl)pyrido[2,3-d]pyrimidine]-3-acetate (Chemical Formula 5)

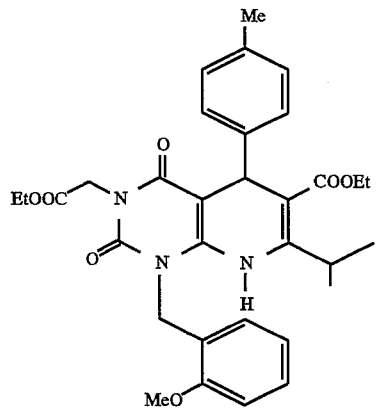

(5)

The compound (0.5 g, 1.5 mmol.) obtained in Reference Example 4 was heated for 90 hours under reflux in ethanol (10 ml) together with p-tolualdehyde (0.54 g, 4.5 mmol.) and ethyl isobutyryl acetate (0.71 g, 4.5 mmol.). The reaction mixture was cooled, then the solvent was distilled off under reduced pressure. The residue was purified by means of a silica gel column chromatography to give 0.2 g (yield 23%) of a yellow amorphous product. The NMR spectrum of thus obtained amorphous compound are as follows.

$^1$H-NMR (200 MHz, CDCl$_3$) δ ppm: 0.80(3H,d), 1.06(3H,d), 1.25(3H,t), 1.26(3H,s), 2.25(3H,s), 3.58(1H,m), 3.96(3H,s), 4.12(2H,q), 4.22(2H,q), 4.62(1H,d), 4.72(1H,d), 5.07(1H,s), 5.22(1H,d), 5.32(1H,d), 6.40(1H,s), 6.90–7.50 (8H,m).

Reference Example 6

The method described as Reference Example 5 was repeated, while employing various aldehydes and ethyl isobutyryl acetates or ethyl acetoacetates. Compounds represented by chemical formula (6) thus obtained were collectively shown in the following Table 3.

TABLE 3

(formula 6)

| Ref. Ex. 6 Cpd. No. | 5-Substit. | 6-Substit. | 7-Substit. | Yield (%) | m.p. (°C.) |
|---|---|---|---|---|---|
| 1 | phenyl | iso-propoxy-carbonyl | methyl | 64 | powder |
| 2 | 4-cyclohexyl-phenyl | ethoxy-carbonyl | iso-propyl | 32 | " |
| 3 | 4-cyclohexyl-phenyl | ethoxy-carbonyl | methyl | 28 | " |
| 4 | 4-cyano-phenyl | ethoxy-carbonyl | " | 42 | " |

Reference Example 7

Production of 5,8-dihydro-2,4-(1H,3H)-dioxo-6-ethoxycarbonyl-7-isopropyl-1-(2-methoxybenzyl)-5-(4-tolyl)pyrido[2,3-d]pyrimidine-3-acetic Acid (Chemical Formula 7)

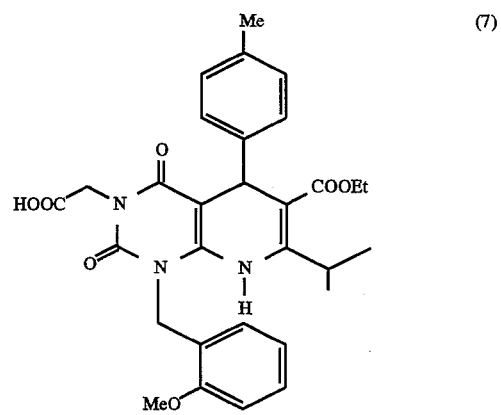

(7)

The compound (0.2 g, 0.35 mmol.) obtained in Reference Example 5 was dissolved in methanol (20 ml). To the solution was added a 2N aqueous solution of sodium hydroxide (2 ml), and the mixture was stirred for 18 hours at room temperature. The reaction mixture was concentrated under reduced pressure, whose pH was adjusted to pH ranging from 2 to 3 with 1N HCl, followed by subjecting to extraction with ethyl acetate to give 0.13 g (yield 68%) of a yellow oily product.

Reference Example 8

Using compounds referred to in Reference Example 6, the method described in Reference Example 7 was repeated. The compounds represented by the chemical formula (8) thus obtained were collectively listed in the following Table 4.

TABLE 4

![Chemical structure 8 with HOOC-CH2-N, carbonyl groups, QR3, R4, R5 substituents on pyrido-pyrimidine with 2-methoxybenzyl group]  (8)

| Ref. Ex. 8 Cpd. No. | 5-Substit. | 6-Substit. | 7-Substit. | Yield (%) | m.p. (°C.) |
|---|---|---|---|---|---|
| 1 | phenyl | iso-propoxy-carbonyl | methyl | 59 | powder |
| 2 | 4-cyclo-hexyl-phenyl | ethoxy-carbonyl | iso-propyl | 57 | " |
| 3 | 4-cyclo-hexyl-phenyl | ethoxy-carbonyl | methyl | 89 | " |
| 4 | 4-cyano-phenyl | " | " | 47 | " |

Reference Example 9

Production of 2,4-(1H,3H)-dioxo-6-2-cyanoethoxycarbonyl)-7-isopropyl-1-(2-methoxybenzyl)-5-(2-quinolyl)pyrido[2,3-d]pyrimidine (Chemical Formula 9)

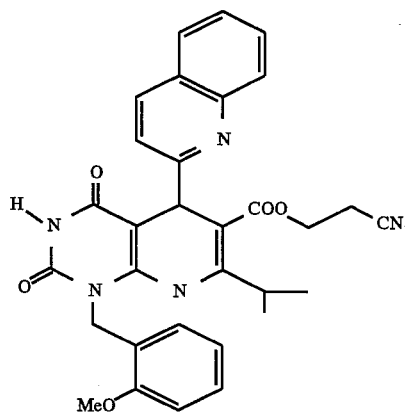

(9)

The compound (3.9 g, 16 mmol.) obtained in Reference Example 2 was stirred in dimethylsufoxide (23 ml) for 25 minutes at 125° C. together with the compound (6.1 g, 19 mmol) obtained by dehydrative condensation of quinoline-2-carboxyaldehyde and 2-cyanoethyl isobutyryl acetate. The reaction mixture was cooled, then poured into ice water. Resulting brownish crystals were collected by filtration and dissolved in ethyl acetate. Washing the solution with water, pale gray powder 4.3 g (yield 49%) was obtained. The compound thus obtained (4.3 g, 7.8 mmol) was dissolved in acetic acid (50 ml), to which was added sodium nitrite (5.9 g). The mixture was stirred for 15 minutes at room temperature. The reaction mixture was poured into ice water, which was subjected to extraction with ethyl acetate. The organic layer was dried and then the solvent was distilled off under reduced pressure. The residue was purified by means of a silica gel column chromatography to give 4.1 g (yield 47%) of a yellow amorphous product. The elemental analysis values were shown in Table 5. The NMR spectrum and IR spectrum of the compound are as follows.

$^1$H-NMR (200 MHz, CDCl$_3$) δ ppm: 1.14(6H,d), 2.12 (2H,t), 3.15(1H,m), 3.89(3H,s), 3.94(2H,t), 5.61(2H,s), 6.80–6.96(3H,m), 7.21(1H,td), 7.53(1H,d), 7.59(1H,td), 7.72(1H,td) 7.88(1H,d), 8.04(1H,d), 8.22(1H,d), 8.77(1H,s).

IR (KBr): 3452, 3196, 3068, 2974, 2254, 1736, 1715, 1603, 1572, 1497 cm$^{-1}$.

TABLE 5

| Elemental Analysis for $C_{31}H_{27}N_5O_5.1.0H_2O$ | | | |
|---|---|---|---|
| | C (%) | H (%) | N (%) |
| Calcd. | 65.60 | 5.15 | 12.34 |
| Found | 65.59 | 5.05 | 12.11 |

Reference Example 10

Using another compounds, the method described in Reference Example 9 was repeated. The compounds represented by the chemical formula (10) thus obtained were collectively listed in the following Table 6.

TABLE 6

![Chemical structure 10]  (10)

| Re. Ex. 10 Cpd. No. | 1-substit. (R$^1$) | 5-substit. (QR$^3$) | 6-substit. (R$^4$) | 7-substit. (R$^5$) | Yield (%) | m.p. (°C.) |
|---|---|---|---|---|---|---|
| 1 | 2-methoxy-benzyl | 4-tolyl | 2-cyanoethoxycarbonyl | isopropyl | 42 | powder |
| 2 | " | 4-methoxy-phenyl | " | " | 19 | " |
| 3 | " | 2-quinolyl | " | methyl | 44 | " |

TABLE 6-continued (10)

| Re. Ex. 10 Cpd. No. | 1-substit. (R¹) | 5-substit. (QR³) | 6-substit. (R⁴) | 7-substit. (R⁵) | Yield (%) | m.p. (°C.) |
|---|---|---|---|---|---|---|
| 4 | " | " | " | phenyl | 46 | " |
| 5 | " | " | " | 3,4-methylene-dioxy-phenyl | 32 | " |
| 6 | 2,4-dimethoxybenzyl | " | " | isopropyl | 83 | " |
| 7 | 3-methoxy-benzyl | " | " | methyl | 26 | " |
| 8 | 2,4-dimethoxybenzyl | " | ethoxycarbonyl | isopropyl | 48 | 208–209 |
| 9 | 2-methoxybenzyl | " | 2-cyanoethoxycarbonyl | normalpropyl | 56 | powder |
| 10 | " | " | " | isobutyl | 55 | 105–107 |
| 11 | " | 2-benzofuranyl | " | isopropyl | 43 | powder |
| 12 | " | 3-methylbenzothienyl | " | " | 36 | " |
| 13 | " | 2-quinolyl | " | ethyl | 72 | " |
| 14 | 2-methoxyphenyl | " | " | isopropyl | 34 | " |
| 15 | 2-methoxybenzyl | 3-quinolyl | " | " | 25 | " |

Reference Example 11

Production of Ethyl [2,4-(1H,3H)-dioxo-5-methylthio-6-ethoxycarbonyl-7-isopropyl-1-(2-methoxybenzyl)pyrido[2,3-d]pyrimidine]-3-acetate (Chemical Formula 11)

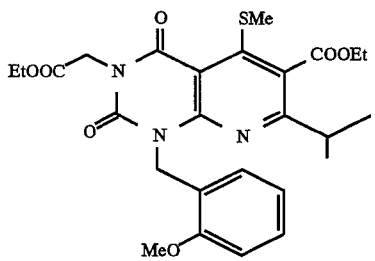

(11)

To a methanol solution (5 ml) containing ethylisobutylylacetate (0.48 g) was added a methanol solution of sodiumu methoxide (28%, 0.58 g) under ice cooling. After stirring for 10 minutes under same condition, to the solution was added dropwise carbon disulfide. After completion of the dropwise addition, dimethyl sulfate (0.75 ml) was added to the reaction mixture. The reaction mixture was stirred at room temperature for 15 minutes. The reaction mixture was poured into water (30 ml), stirred for 5 minutes, which was then subjected to extraction with isopropyl ether to give a yellow oily product (0.40 g).

A mixture of the the oily product, the compound obtained in Reference Example 4 (0.50 g, 1.5 mmol) and potassium carbonate (0.31 g) was stirred in dimethylformamide (10 ml) for 5 hours at 150° C. The reaction mixture was, after cooling, concentrated to dryness, to which were added a saturated aqueous solution of ammonium chloride (20 ml) and ethyl acetate (20 ml), and then the mixture was stirred. The organic layer was separated. The aqueous layer was subjected to extraction with ethyl acetate (20 ml). The extract was combined with the organic layer, which was then dried. The solvent was distilled off under reduced pressure. The residue was purified by means of a silica gel column chromatography to give 0.06 g (yield 8%) of a yellow amorphous product. The NMR spectrum and MS spectrum of thus obtained yellow amorphous compound was as follows.

¹H-NMR (200 MHz, CDCl₃) δ ppm: 1.28(3H,t), 1.35(6H, d), 1.41(3H,t), 2.21(3H,s), 3.86(3H,s), 4.20(2H,q), 4.40(2H, q), 4.40–4.60(1H,m), 4.84(2H,s), 5.59(2H,s), 6.7–7.0(3H, m), 7.15–7.3(1H,m).

MS, m/z: 530(MH)⁺

Reference Example 12

Production of Ethyl [1,3,7,13-tetraoxo-1,2,3,4,7,13-hexahydro-6-isopropyl-pyrimido[4",5":6',5']pyrido[3',4':4,3]pyrrolo[1,2-a]quinoline]-3-acetate (Chemical Formula 12)

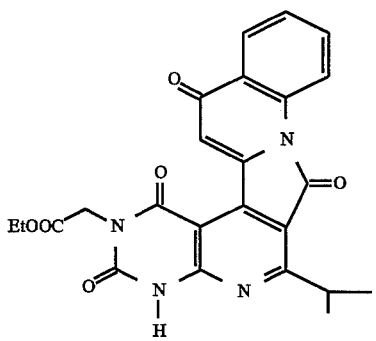

(12)

The compound (1.10 g, 2.38 mmol.) obtained in Example 17 (Compound No. 16) was dissolved in dichloromethane (100 ml). To the solution was added thionyl chloride (0.87 ml, 11.89 mmol), and the mixture was stirred for 2 hours at room temperature. 20 ml of toluene was added to the reaction mixture, and then concentrated under reduced pressure. The residue was dissolved in dichloromethane, and then filtered with sellaite. The filtrate was concentrated, and the residue thus obtained was washed with ethyl acetate to give 0.30 g (yield 28%) of a yellow powdery product. The elemental analysis values were shown in Table 7. The NMR spectrum, IR spectrum and MS spectrum of the compound are as follows.

¹H-NMR (500 MHz, DMSO-d₆) δ ppm: 1.32–1.41(9H, m), 4.28(2H,q), 4.37(1H,m), 4.82(2H,s), 7.47(1H,t), 7.78 (1H,t), 8.30(1H,d), 8.64(1H,s), 8.78(1H,s), 9.19(1H,d)

IR (KBr): 1738, 1682, 1642, 1576, 1477, 1396 cm$^{-1}$.
FAB-MS, m/z: 461.1(MH)$^+$

TABLE 7

Elemental Analysis for $C_{24}H_{20}N_4O_6 \cdot 0.3H_2O \cdot 0.2C_4H_8O_2$

|  | C (%) | H (%) | N (%) |
|---|---|---|---|
| Calcd. | 61.62 | 4.62 | 11.58 |
| Found | 61.41 | 4.32 | 11.40 |

Reference Example 13

Production of Ethyl [1,3,7,13-tetraoxo-1,2,3,4,7,13-hexahydro-6-isopropyl-4-(2-methylthiobenzyl)pyrimido[4",5":6',5']pyrido[3',4':4,3]pyrrolo[1,2-a]quinoline]-3-acetate (Chemical Formula 13)

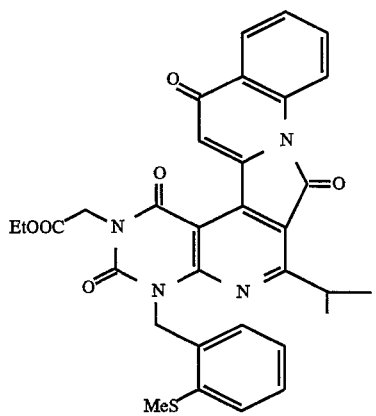

(13)

A dimethylformamide (5 ml) solution containing the compound (0.20 g, 0.43 mmol.) obtained in Reference Example 12, 2-methylthio benzylchloride (0.74 g, 4.30 mmol) and potassium hydrogen carbonate (0.07 g, 0.64 mmol) was stirred for 2 days at room temperature. To the reaction mixture was added and a saturated aqueous solution of ammonium chloride, which was subjected to distribution to dichloromethane and a saturated aqueous solution of sodium chloride. The organic layer was dried with MgSO$_4$ and then the solvent was distilled off under reduced pressure.

The residue was purified by means of a silica gel column chromatography to give 0.21 g (yield 80%) of a yellow powdery product.

The elemental analysis values were shown in Table 8. The NMR spectrum, IR spectrum and MS spectrum of the compound are as follows.

$^1$H-NMR (200 MHz, CDCl$_3$) δ ppm: 1.14(6H,d), 1.34(3H,t), 2.57(3H,s), 4.23–4.34(3H,m), 4.93(2H,s), 5.76(2H,s), 6.83(1H,d), 7.03(1H,t), 7.22–7.35(2H,m), 7.47(1H,t), 7.77 (1H,t), 8.32(1H,d), 8.84(1H,s), 9.18(1H,d).

IR (KBr): 1725, 1680, 1640, 1578, 1475 cm$^{-1}$.
FAB-MS, m/z: 597.1(MH)$^+$

TABLE 8

Elemental Analysis for $C_{32}H_{28}N_4O_8S \cdot 0.8H_2O$

|  | C (%) | H (%) | N (%) |
|---|---|---|---|
| Calcd. | 62.89 | 4.88 | 9.16 |
| Found | 63.14 | 4.67 | 8.88 |

Reference Example 14

Using compounds referred to in Reference Example 12, the method described in Reference Example 13 was repeated. The compounds represented by the chemical formula (14), thus obtained, were collectively listed in the following Table 9.

TABLE 9

(14)

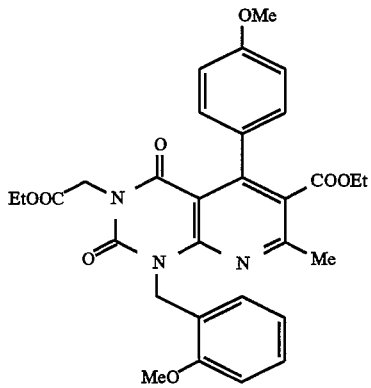

| Ref. Ex. 14 Cpd. No. | 1-substit. (R$^1$) | 7-substit. (R$^5$) | Yield (%) | m.p. (°C.) |
|---|---|---|---|---|
| 1 | 2,3-dimethoxybenzyl | isopropyl | 71 | 258–259 |
| 2 | 2,3,4-trimethoxybenzyl | isopropyl | 72 | 209–210 |

Example 1

Production of Ethyl [2,4(1H,3H)-dioxo-6-ethoxycarbonyl-7-methyl-1-(2-methoxybenzyl)-5-(4-methoxyphenyl)pyrido[2,3-d]pyrimidine]-3-acetate (Chemical Formula 15)

(15)

The compound (2.1 g, 6.3 mmol.) obtained in Reference Example 4 was heated for 130 hours under reflux in ethanol (40 ml) together with p-anisaldehyde (0.81 g, 6.0 mmol.) and ethyl acetoacetate (0.79 g, 6.1 mmol.). The reaction mixture was cooled, then the solvent was distilled off under reduced pressure. The residue was purified by means of a silica gel column chromatography to give 2.6 g (yield 70%) of a yellow amorphous product. The amorphous compound (2.3 g, 4.1 mmol.) was dissolved in acetic acid (50 ml), to which was added sodium nitrite (2.0 g). The mixture was stirred for one hour at room temperature. The reaction mixture was poured into ice-water, which was subjected to extraction with ethyl acetate (100 ml each, twice). The organic layer was dried, and then the solvent was distilled off under reduced pressure. The residue was purified by means of a silica gel column chromatography to give 1.8 g (yield 77%) of a yellow oily product. The NMR spectrum of this product was as follows.

$^1$H-NMR (200 MHz, CDCl$_3$) δ ppm: 0.97(3H,t), 1.22(3H, t), 2.51(3H,s), 3.84(3H,s), 3.90(3H,s), 3.98(2H,q), 4.15(2H, q), 4.71(2H,s), 5.65(2H, s), 6.75–7.61(8H,m).

Example 2

Using suitable aldehyde instead of p-anisaldehyde and ethyl isobutyryl acetate or ethyl acetoacetate, the method described in Example 1 was repeated to give corresponding compounds of chemical formula 16, which were listed in Table 10.

TABLE 10

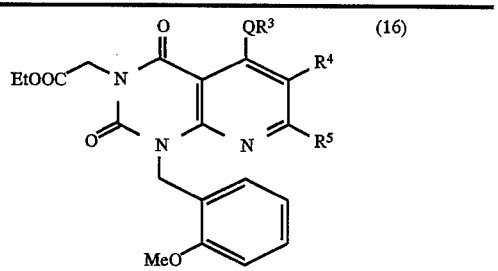

(16)

| Ex. 2 Cpd. No. | 5-substit. | 6-substit. | 7-substit. | Yield (%) | m.p. (°C.) |
|---|---|---|---|---|---|
| 1 | 2-methoxyphenyl | ethoxycarbonyl | methyl | 44 | powder |
| 2 | 2-tolyl | ethoxycarbonyl | " | 76 | " |
| 3 | 2-bromophenyl | ethoxycarbonyl | " | 48 | " |
| 4 | 2-nitrophenyl | ethoxycarbonyl | " | 59 | " |
| 5 | 3-methoxyphenyl | ethoxycarbonyl | " | 67 | " |
| 6 | 3-tolyl | ethoxycarbonyl | " | 43 | " |
| 7 | 3-bromophenyl | ethoxycarbonyl | " | 58 | " |
| 8 | 3-nitrophenyl | ethoxycarbonyl | " | 35 | " |
| 9 | 3-cyanophenyl | ethoxycarbonyl | " | 55 | " |
| 10 | 4-tolyl | ethoxycarbonyl | " | 73 | " |
| 11 | 4-bromophenyl | ethoxycarbonyl | " | 55 | " |
| 12 | 4-nitrophenyl | ethoxycarbonyl | " | 73 | " |
| 13 | 4-biphenyl | ethoxycarbonyl | " | 61 | " |
| 14 | 1-naphthyl | ethoxycarbonyl | " | 43 | " |
| 15 | 2-naphthyl | ethoxycarbonyl | " | 22 | " |
| 16 | 4-pyridyl | ethoxycarbonyl | " | 68 | " |
| 17 | 3-pyridyl | ethoxycarbonyl | " | 69 | " |
| 18 | 2-pyridyl | ethoxycarbonyl | " | 28 | " |
| 19 | 6-methyl-2-pyridyl | ethoxycarbonyl | " | 38 | " |
| 20 | 3-quinolinyl | ethoxycarbonyl | " | 34 | " |
| 21 | 4-quinolinyl | ethoxycarbonyl | " | 58 | " |
| 22 | 2-thienyl | ethoxycarbonyl | " | 50 | " |
| 23 | 3-thienyl | ethoxycarbonyl | " | 44 | " |
| 24 | 3-methyl-2-thienyl | ethoxycarbonyl | " | 44 | " |
| 25 | 5-methyl-2-thienyl | ethoxycarbonyl | " | 63 | " |
| 26 | 3-qunolyl | ethoxycarbonyl | isopropyl | 33 | " |
| 27 | 3,4-dimethoxyphenyl | ethoxycarbonyl | " | 47 | " |
| 28 | 4-methoxyphenyl | ethoxycarbonyl | isopropyl | 12 | " |
| 29 | 4-methoxyphenyl | ethoxycarbonyl | phenyl | 27 | " |
| 30 | 4-methoxyphenyl | cyclopentyloxycarbonyl | isobutyl | 58 | " |
| 31 | 3,4-dimethoxyphenyl | ethoxycarbonyl | isopropyl | 37 | " |
| 32 | 3,3-methylenedioxyphenyl | ethoxycarbonyl | isopropyl | 52 | " |

Example 3

Production of t-Butyl [2,4(1H,3H)-dioxo-6-(2-cyanoethoxycarbonyl)-7-isopropyl-1-(2-methoxybenzyl)-5-(2-quinolyl)pyrido[2,3-d]pyrimidine]-3-acetate (Chemical Formula 17)

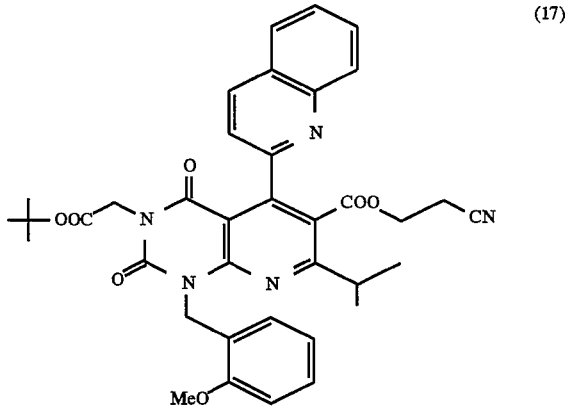

(17)

The compound (1.0 g, 1.9 mmol.) obtained in Reference Example 9 was stirred for 40 minutes at room temperature in dimethylformamide (5 ml) together with tert-butyl bromoacetate (0.88 ml, 5.6 mmol) and potassium carbonate (0.76 g, 5.6 mmol). The reaction mixture was adjusted to pH ranging from 1 to 2 with 1N HCl, which was subjected to distribution to ethyl acetate and water. The organic layer was dried, then the solvent was distilled off under reduced pressure. The residue was purified by means of a silica gel column chromatography to give 0.51 g (yield 41%) of a yellow amorphous product. The elemental analysis values of the compound thus obtained were shown in Table 11. The NMR spectrum and IR spectrum of the compound are as follows.

TABLE 11

| Elemental Analysis for $C_{37}H_{37}N_5O_7$ | | | |
|---|---|---|---|
| | C (%) | H (%) | N (%) |
| Calcd. | 66.96 | 5.62 | 10.55 |
| Found | 66.77 | 5.74 | 10.51 |

$^1$-NMR (200 MHz, CDCl$_3$) δ ppm: 1.15(6H,d), 1.40(9H, s), 2.14(2H,t), 3.15(1H,m), 3.90(2H,s), 3.94(2H,t), 4.59(2H, s), 5.69(2H,s), 7.22(1H,td), 7.54(1H,d), 7.60(1H,td) 7.73 (1H,td), 7.88(1H,d), 8.04(1H,d), 8.22(1H,d).

IR (KBr): 3452, 2976, 2938, 2364, 2258, 1742, 1721, 1678, 1603, 1574 cm$^{-1}$.

Example 4

Using the corresponding compound for starting material, the method described in Example 3 was repeated to give compounds of chemical formula 18, which were listed in Table 12.

Example 5

Production of Ethyl [2,4(1H,3H)-dioxo-6-(2-cyanoethoxycarbonyl)-7-isopropyl-5-(2-quinolyl) pyrido[2,3-d]pyrimidine]-3-acetate (Chemical Formula 19)

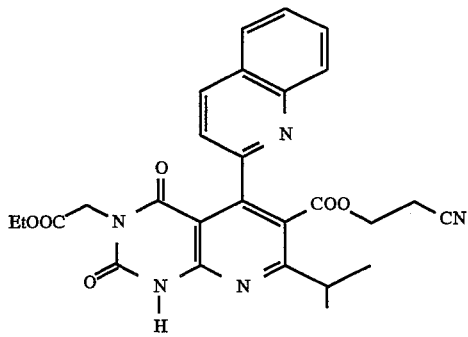

(19)

The compound (Compound No. 10; 10.0 g, 15.0 mmol.) obtained in Example 4 was dissolved in aceton-water (1:1 v/v, 600 ml). To the solution was added cerium(IV) ammonium nitrate (24.7 g, 45.0 mmol), and the mixture was stirred for one hour at room temperature. The reaction mixture was concentrated into ½ volume, and the residue was subjected to extraction with ethyl acetate. The organic layer was dried (with Na$_2$SO$_4$), and the solvent was distilled off under reduced pressure. The residue was purified by

TABLE 12

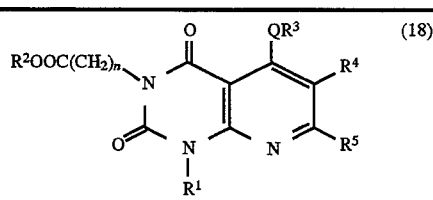

(18)

| Ex. 4 Cpd. No. | 1-substit. (R$^1$) | n | R$^2$ | 5-substit. (QR$^3$) | 6-substit. (R$^4$) | 7-substit. (R$^5$) | Yield (%) | m.p. (°C.) |
|---|---|---|---|---|---|---|---|---|
| 1 | 2-methoxy-benzyl | 1 | t-butyl | 4-tolyl | 2-cyanoethoxy- | iso-propyl | 64 | powder |
| 2 | " | 1 | ethyl | 4-methoxy-phenyl | " | " | 74 | " |
| 3 | " | 3 | " | " | " | " | 48 | " |
| 4 | " | 1 | t-butyl | 2-quinolyl | " | methyl | 87 | " |
| 5 | " | 1 | ethyl | " | " | iso-propyl | 86 | " |
| 6 | " | 3 | " | " | " | " | 43 | " |
| 7 | " | 1 | t-butyl | " | " | phenyl | 53 | " |
| 8 | " | 1 | " | " | " | 3,4-methylene-dioxyphenyl | 86 | " |
| 9 | " | 1 | ethyl | " | " | methyl | 69 | " |
| 10 | 2,4-dimethoxy-benzyl | 1 | " | " | " | iso-propyl | 70 | " |
| 11 | 2,4-dimethoxy-benzyl | 1 | t-butyl | " | " | " | 78 | " |
| 12 | " | 1 | ethyl | " | ethoxycarbonyl | " | 73 | " |
| 13 | 2-methoxy-benzyl | 1 | " | " | 2-cyanoethoxy-carbonyl | normal-propyl | 74 | " |
| 14 | " | 1 | " | " | 2-cyanoethoxy-carbonyl | iso-butyl | 77 | 164–165 |
| 15 | " | 1 | " | 2-benzofuranyl | 2-cyanoethoxy-carbonyl | iso-propyl | 77 | powder |
| 16 | " | 1 | " | 3-methyl-2-benzothienyl | 2-cyanoethoxy-carbonyl | " | 84 | " |
| 17 | " | 1 | " | 2-quinolyl | 2-cyanoethoxy-carbonyl | ethyl | 86 | " |
| 18 | 2-methoxy-phenyl | 1 | t-butyl | " | 2-cyanoethoxy-carbonyl | iso-propyl | 89 | " |
| 19 | 2-methoxy-benzyl | 1 | ethyl | " | 2-cyanoethoxy-carbonyl | " | 79 | " | means of a silica gel column chromatography to give 4.59 g (yield 46%) of yellow powdery products. The elemental analysis values were shown In Table 13. The NMR spectrum and IR spectrum of thus obtained compound are as follows.

TABLE 13

| Elemental Analysis for $C_{27}H_{25}N_5O_6.0.5H_2O$ | | | |
|---|---|---|---|
| | C (%) | H (%) | N (%) |
| Calcd. | 61.82 | 4.99 | 13.35 |
| Found | 61.88 | 5.23 | 12.64 |

$^1$H-NMR (200 MHz, CDCl$_3$) δ ppm: 1.21(3H, t), 1.35 (6H,d), 2.17(2H,t), 3.25(1H,m), 3.97(2H,t), 4.15(2H,q), 4.61(2H,s), 7.53(1H,d), 7.61(1H,t), 7.74(1H,t), 7.89(1H,d), 8.05(1H,d), 8.23(1H,d), 8.56(1H,s).

IR (KBr): 3424, 3264, 2976, 2362, 1734, 1680, 1620, 1578, 1504 cm$^{-1}$.

Example 6

Production of Ethyl [2,4(1H,3H)-dioxo-6-(2-cyanoethoxycarbonyl)-7-isopropyl-5-(2-quinolyl) pyrido[2,3-d]pyrimidine]-3-acetate
(Chemical Formula 20)

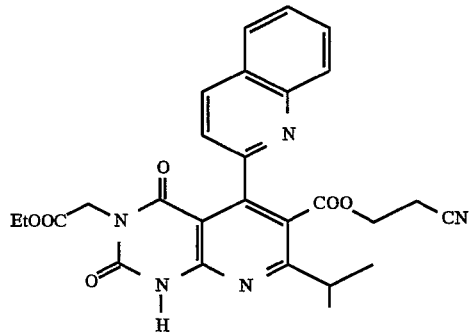
(20)

The solution of the compound (Compound No.10; 9.1 g, 13.7 mmol.) obtained in Example 4 in trifluoroacetic acid (50 ml) was stirred for 4 hours at 60° C. The reaction mixture was concentrated to remove trifluoroacetic acid, and the residue was subjected to distribution in ethyl acetate-aqueous solution of sodium chloride. The organic layer was dried (with MgSO$_4$), and the solvent was distilled off under reduced pressure. The residue was purified by means of a silica gel column chromatography to give 6.47 g (yield 92%) of yellow powdery products.

Example 7

Using the compound obtained in Example 4 (Compound No. 12), the method described in Example 5 was repeated to give the compound represented by the Chemical Formula 21).

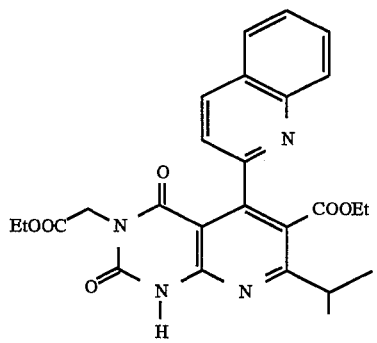
(21)

Example 8

Production of Ethyl [2,4(1H,3H)-dioxo-6-(2-cyanoethoxycarbonyl)-7-isopropy-1-methyl-5-(2-quinolyl)pyrido[2,3-d]pyrimidine]-3-acetate
(Chemical Formula 22)

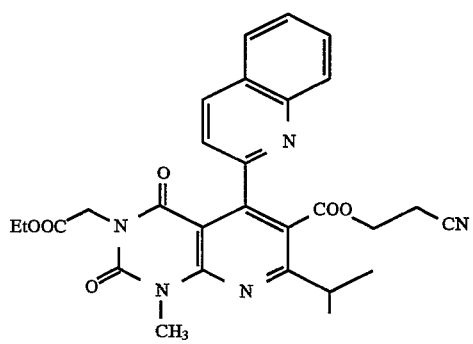
(22)

The compound (1.78 g, 3.5 mmol.) obtained in Example 5, methyl iodide (0.98 g, 6.9 mmol) and pottasium crbonate (1.42 g, 10.4 mmol) were dissolved in dimethylformamide (70 ml). To the solution was added 1N HCl, and was subjected to distribution in ethyl acetate-water. The organic layer was dried (with Na$_2$SO$_4$), and the solvent was distilled off under reduced pressure. The residue was purified by means of a silica gel column chromatography to give 1.42 g (yield 78%) of yellow bubbly products. The elemental analysis values were shown in Table 14. The NMR spectrum and IR spectrum of thus obtained compound are as follows.

TABLE 14

| Elemental Analysis for $C_{28}H_{27}N_5O_6.0.1H_2O$ | | | |
|---|---|---|---|
| | C (%) | H (%) | N (%) |
| Calcd. | 63.12 | 5.10 | 13.23 |
| Found | 63.29 | 5.15 | 13.18 |

$^1$H-NMR (200 MHz, CDCl$_3$) δ ppm: 1.21(3H,t), 1.39(6H, d), 2.14(1H,t), 3.30(1H,m), 3.82(3H,s), 3.96(2H,t), 4.15(2H, q), 4.65 (2H,s), 7.50(1H,d), 7.59(1H,t), 7.73(1H,t), 7.88(1H, d), 8.03(1H,d), 8.21(1H,d).

IR (KBr): 3452, 2974, 2364, 1742, 1719, 1673, 1620, 1601, 1574, 1506 cm$^{-1}$.

Example 9

Using the corresponding compounds as starting material, the method described in Example 8 was repeated to give the compound represented by the Cemical Formula (23), which has various 1-position substituents. Compounds thus obtained were collectively shown In the following Table 15.

TABLE 15

(23)

[Chemical structure showing pyrido[2,3-d]pyrimidine with quinolyl group, EtOOC, COOEt, isopropyl, and R¹ substituents]

| Ex. 9 Cpd. No. | 1-substituent (R¹) | Yield (%) | m.p. (°C.) |
|---|---|---|---|
| 1 | 2-quinolylmethyl | 97 | powder |
| 2 | 2-methoxyphenetyl | 92 | " |
| 3 | 3-indolylethyl | 62 | " |

Example 10

Production of 2,4(1H,3H)-dioxo-6-ethoxycarbonyl-7-isopropyl-1-(2-methoxbenzyl)-5-(4-tolyl)pyrido[2,3-d]pyrimidine-3-acetic Acid
(Chemical Formula 24)

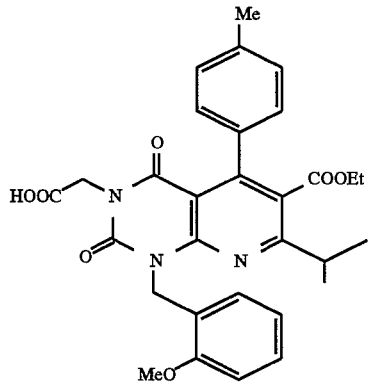

(24)

The compound (0.13 g, 0.24 mmol.) obtained in Reference Example 7 was dissolved in acetic acid (20 ml). To the solution was added sodium nitrite (0.1 g), and the mixture was stirred for one hour at room temperature. The reaction mixture was poured into ice-water, which was subjected to extraction with ethyl acetate (20 ml each, three times). The organic layer was dried, and the solvent was distilled off under reduced pressure. The residue was purified by means of a silica gel column chromatography. Crude crystals thus obtained were recrystallized from ethyl acetate-isopropyl ether (1:2) to give 0.06 g (yield 54%) of yellow powdery crystals, m.p.190°–192° C. (decomp.). The elemental analysis values were shown in Table 16. The NMR spectrum and IR spectrum of thus obtained compound are as follows.

TABLE 16

Elemental Analysis for $C_{30}H_{31}N_3O_7 \cdot 2H_2O$

|  | C (%) | H (%) | N (%) |
|---|---|---|---|
| Calcd. | 61.95 | 6.07 | 7.22 |
| Found | 61.77 | 5.80 | 7.12 |

$^1$H-NMR (200 MHz, CDCl$_3$) δ ppm: 0.89(3H, t), 1.08 (6H,d), 2.25(3H,s), 2.9–3.1(1H,m), 3.41(3H,s), 3.90(2H,q), 4.41(2H,s), 5.53(2H,s), 6.6–7.2(8H,m).

IR (KBr): 3456, 1717, 1671, 1562, 1518, 1495, 1466, 1386, 1371, 1305, 1247 cm$^{-1}$.

Example 11

Using compounds reffered to in Reference Example 8, the method described in Example 10 was repeated. The compounds thus obtained (Chemical Formula 25) were listed in Table 17.

TABLE 17

(25)

[Chemical structure with QR³, R⁴, R⁵ substituents on pyrido[2,3-d]pyrimidine, HOOC-CH₂-N, and MeO-benzyl group]

| Ex. 11 Cpd. No. | 5-substit. (QR³) | 6-substit. (R⁴) | 7-substit. (R⁵) | Yield (%) | m.p. (°C.) |
|---|---|---|---|---|---|
| 1 | phenyl | iso-propoxy-carbonyl | methyl | 50 | 215–220 |
| 2 | 4-cyclohexylphenyl | ethoxy-carbonyl | iso-propyl | 55 | powder |
| 3 | 4-cyclohexylphenyl | ethoxy-carbonyl | methyl | 38 | " |
| 4 | 4-cyano-phenyl | ethoxy-carbonyl | " | 46 | 155–158 |

Example 12

Production of 2,4(1H,3H)-dioxo-6-ethoxycarbonyl-7-methyl-1-(2-methoxybenzyl)-5-(4-methoxyphenyl) pyrido[2,3-d]pyrimidine-3-acetic Acid
(Chemical Formula 26)

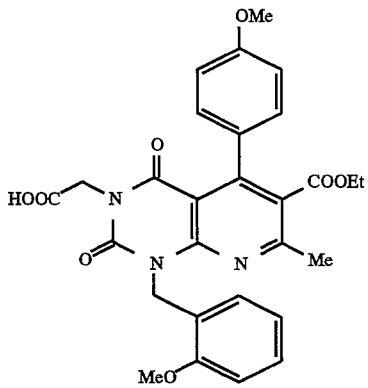

(26)

The compound (Compound No. 10: 1.5 g, 2.6 mmol.) obtained in Example 2 was dissolved in methanol (30 ml), to which was added a 2N aqueous solution of sodium hydroxide (2.6 ml), and the mixture was stirred for 20 hours at room temperature. The reaction mixture was concentrated under reduced pressure. The concentrate was adjusted to pH ranging from 2 to 3 with 1N HCl, which was subjected to extraction with ethyl acetate. The extract was purified by means of a silica gel column chromatography to give crude crystals, followed by recrystallization from isopropyl alcohol to give 0.63 g (yield 46%) of yellow powdery crystals, m.p. 190°–192° C. Elemental analysis of the product is shown in Table 18. The NMR spectrum and IR spectrum of the compound were as follows.

TABLE 18

Elemental Analysis for $C_{28}H_{27}N_3O_8.2.25H_2O$

|  | C (%) | H (%) | N (%) |
|---|---|---|---|
| Calcd. | 58.58 | 5.53 | 7.32 |
| Found | 58.73 | 5.22 | 7.31 |

$^1$H-NMR (200 MHz, CDCl$_3$) δ ppm: 0.88(3H,t), 2.39(3H, s), 3.79(3H,s), 3.89(3H,s), 3.92(2H,q), 4.18(2H,s), 5.47(2H, s), 6.78(1H,t), 6.68(1H,d), 6.91(2H,d), 7.01(1H,d), 7.06(2H, d), 7.20(1H,t).

IR (KBr): 3450, 1717, 1669, 1609, 1564, 1518, 1483, 1381, 1278, 1247 cm$^{-1}$.

Example 13

Using compounds reffered to in Example 2 (except Compound No. 19), Example 7 and Example 9, the method described in Example 12 was repeated. Compounds thus obtained (Chemical Formula 27) are listed in Table 19.

TABLE 19

(27)

| Ex. 13 Cpd. No. | 1-substit. (R$^1$) | 5-substit. (QR$^3$) | 7-substit. (R$^5$) | Yield (%) | m.p. (°C.) |
|---|---|---|---|---|---|
| 1 | 2-methoxybenzyl | 2-methoxyphenyl | methyl | 44 | powder |
| 2 | 2-methoxybenzyl | 2-tolyl | " | 45 | " |
| 3 | 2-methoxybenzyl | 2-bromophenyl | " | 65 | 214–216 |
| 4 | 2-methoxybenzyl | 2-nitrophenyl | " | 44 | 212–214 |
| 5 | 2-methoxybenzyl | 3-methoxyphenyl | " | 51 | 192–194 |
| 6 | 2-methoxybenzyl | 3-tolyl | " | 54 | powder |
| 7 | 2-methoxybenzyl | 3-bromophenyl | " | 51 | 214–216 |
| 8 | 2-methoxybenzyl | 3-nitrophenyl | " | 66 | 224–226 |
| 9 | 2-methoxybenzyl | 3-cyanophenyl | " | 61 | 226–228 |
| 10 | 2-methoxybenzyl | 4-methoxyphenyl | " | 46 | powder |
| 11 | 2-methoxybenzyl | 4-tolyl | " | 35 | 204–206 |
| 12 | 2-methoxybenzyl | 4-bromophenyl | " | 62 | 208–210 |
| 13 | 2-methoxybenzyl | 4-nitrophenyl | " | 55 | powder |
| 14 | 2-methoxybenzyl | 4-biphenyl | " | 63 | " |
| 15 | 2-methoxybenzyl | 1-naphthyl | " | 36 | 206–208 |
| 16 | 2-methoxybenzyl | 2-naphthyl | " | 89 | powder |
| 17 | 2-methoxybenzyl | 4-pyridyl | " | 64 | " |
| 18 | 2-methoxybenzyl | 3-pyridyl | " | 53 | " |
| 19 | 2-methoxybenzyl | 6-methyl-2-pyridyl | " | 93 | " |
| 20 | 2-methoxybenzyl | 3-quinolyl | " | 79 | " |
| 21 | 2-methoxybenzyl | 4-quinolyl | " | 66 | " |
| 22 | 2-methoxybenzyl | 2-thienyl | " | 53 | 202–204 |
| 23 | 2-methoxybenzyl | 3-thienyl | " | 53 | powder |
| 24 | 2-methoxybenzyl | 3-methyl-2-thienyl | " | 48 | " |
| 25 | 2-methoxybenzyl | 5-methyl-2-thienyl | " | 71 | " |
| 26 | hydrogen atom | 2-quinolyl | isopropyl | 55 | 135–137 |
| 27 | 2-quinolylmethyl | " | isopropyl | 57 | >300 |
| 28 | 2-methoxyphenyl | " | isopropyl | 100 | 163–164 |
| 29 | 3-indolethyl | " | isopropyl | 73 | 210–212 |

Example 14

Production of 2,4(1H,3H)-dioxo-6-carboxy-7-isopropyl-1-(2-methoxybenzyl)-5-(2-quinolyl)pyrido[2,3-d]pyrimidine-3-acetic Acid (Chemical Formula 28)

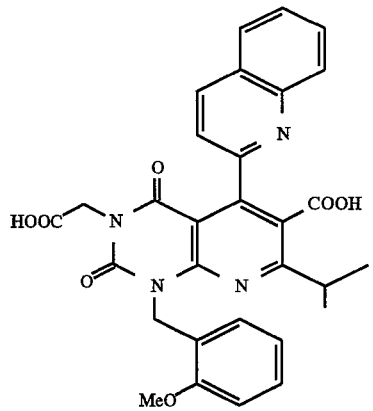

(28)

The compound (Compound No. 5: 0.20 g, 0.31 mmol.) obtained in Example 4 was dissolved in the mixture of methanol (1.0 ml) and 1,4-dioxane (2.0 ml) to which was added a 1N aqueous solution of sodium hydroxide (0.63 ml, 1.3 mmol), and the mixture was stirred for 30 minutes at room temperature. The reaction mixture was adjusted to pH ranging from 1 to 2 with 1N HCl, which was subjected to distribution to ethyl acetate and water. The organic layer was washed by a saturated aqueous solution of sodium chloride, and dried, then the solvent was distilled off under reduced pressure. The residue was recrystallized from isopropyl ether to give 0.12 g (yield 71%) of pale yellow powdery crystals, m.p. over 300° C. Elemental analysis of the product is shown in Table 20. The NMR spectrum and IR spectrum of the compound were as follows.

TABLE 20

Elemental Analysis for $C_{30}H_{26}N_4O_7 \cdot 0.75H_2O$

| | C (%) | H (%) | N (%) |
|---|---|---|---|
| Calcd. | 63.43 | 4.88 | 9.86 |
| Found | 63.45 | 4.66 | 9.73 |

$^1$H-NMR (200 MHz, DMSO-$d_6$) δ ppm: 1.05(6H,d), 3.19(1H,m), 3.90(3H,s), 4.47(2H,s), 5.55(2H,s), 6.83(1H,t), 6.93(1H,d), 7.05(1H,d), 7.24(1H,dd), 7.52(1H,d), 7.65(1H,dd), 7.77(1H,dd), 7.93(1H,d), 8.02(1H,dd), 8.32(1H,d), 12.97(2H,br).

IR (KBr): 3480, 2980, 1715, 1671, 1576, 1493, 1464 cm$^{-1}$.

Example 15

Using compounds reffered to in Example 4, the method described in Example 14 was repeated. Compounds thus obtained (Chemical Formula 29) are listed in Table 21.

TABLE 21

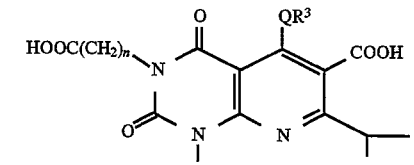

(29)

| Ex. 15 Cpd. No. | 1-substit. (R$^1$) | n | 5-substit. (QR$^3$) | Yield (%) | m.p. (°C.) |
|---|---|---|---|---|---|
| 1 | 2-methoxy-benzyl | 1 | 4-tolyl | 53 | 245–247 |
| 2 | 2-methoxy-benzyl | 1 | 4-methoxy-phenyl | 71 | 123–125 |
| 3 | 2-methoxy-benzyl | 3 | 4-methoxy-phenyl | 84 | 150–152 |
| 4 | 2,4-di-meth-oxy-benzyl | 1 | 2-quinolyl | 61 | 274–282 |
| 5 | 2-methoxy-phenethyl | 1 | " | 84 | 292–293 |
| 6 | methyl | 1 | " | 75 | 259–260 |
| 7 | 2-methoxy-benzyl | 1 | 2-benzo-furanyl | 90 | 248–249 |
| 8 | 2-methoxy-benzyl | 1 | 3-methyl-2-benzothienyl | 85 | 144–145 |
| 9 | 2-methoxy-benzyl | 1 | 3-quinolyl | 61 | 203–204 |

Example 16

Production of t-Butyl [2,4(1H,3H)-dioxo-6-carboxy-7-isopropyl-1-(2-methoxybenzyl)-5-(2-quinolyl)pyrido[2,3-d]pyrimidine]-3-acetate (Chemical Formula 30)

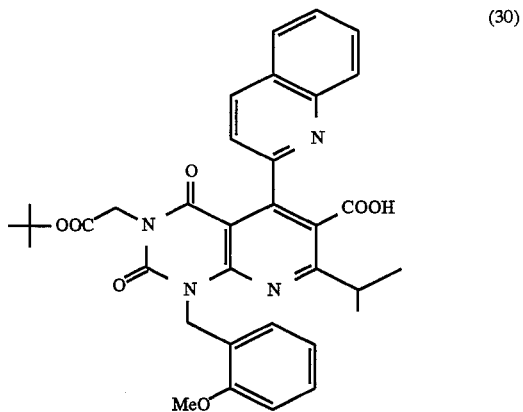

(30)

The compound (2.9 g, 4.3 mmol.) obtained in Example 3 was dissolved in the mixture of methanol (130 ml) and water (17 ml), to which was added a 2N aqueous solution of potassium carbonate (8.6 ml, 8.6 mmol), and the mixture was stirred for 1 hour at room temperature. The reaction mixture was adjusted to pH ranging from 2 to 3 with 1N HCl, which was subjected to distribution to ethyl acetate and water. The organic layer was washed by a saturated aqueous solution of sodium chloride, and dried, then the solvent was distilled off under reduced pressure. The residue was was purified by means of a silica gel column chromatography to give 2.3 g (yield 87%) of yellow powdery crystals, m.p. over 300° C. Elemental analysis of the product is shown in Table 22. The NMR spectrum and IR spectrum of the compound were as follows.

$^1$H-NMR (200 MHz, DMSO-$d_6$) δ ppm: 1.05(6H,d), 1.34(9H,s), 3.19(1H,m), 3.90(3H,s), 4.45(2H,s), 5.54(2H,s), 6.83–6.92(2H,m), 7.06(1H,d), 7.24(1H,td), 7.53(1H,d), 7.65 (1H,t), 7.77(1H,t), 7.94(1H,d), 8.04(1H,d), 8.33(1H,d).

IR (KBr): 3454, 2972, 2928, 2366, 1719, 1678, 1605, 1572, 1495 cm$^{-1}$.

TABLE 22

Elemental Analysis for $C_{34}H_{34}N_4O_7 \cdot 0.25H_2O$

|  | C (%) | H (%) | N (%) |
|---|---|---|---|
| Calcd. | 66.38 | 5.65 | 9.11 |
| Found | 66.30 | 5.61 | 8.92 |

Example 17

Using compounds reffered to in Example 4 and others, the method described in Example 16 was repeated. Compounds thus obtained (Chemicl Formula 31) are listed in Table 23.

TABLE 23

(structure 31: HOOC(CH$_2$)$_n$-N with pyridine ring bearing QR$^3$, COOH, R$^5$, and N-R$^1$ substituents)

| Ex. 17 Cpd. No. | 1-substit. (R$^1$) | n | R$^2$ | 5-substit. (QR$^3$) | 7-substit. (R$^5$) | Yield (%) | m.p. (°C.) |
|---|---|---|---|---|---|---|---|
| 1 | 2-methoxy-benzyl | 1 | ethyl | 2-quinolyl | isopropyl | 88 | 230–231 |
| 2 | " | 3 | " | " | " | 48 | 158–159 |
| 3 | " | 1 | t-butyl | " | methyl | 77 | >300 |
| 4 | " | 1 | " | " | phenyl | 73 | 175–177 |
| 5 | " | 1 | " | " | 3,4-methylene-dioxy-phenyl | 98 | >300 |
| 6 | 2,4-dimethoxybenzyl | 1 | ethyl | " | isopropyl | 69 | 184–186 |
| 7 | methyl | 1 | " | " | " | 72 | 219–221 |
| 8 | 2-methoxyphenethyl | 1 | " | " | " | 87 | 219–220 |
| 9 | 2-methoxybenzyl | 1 | " | " | normalpropyl | 84 | 163–165 |
| 10 | " | 1 | " | " | isobutyl | 94 | 218–220 |
| 11 | " | 1 | " | 2-benzofuranyl | isopropyl | 88 | 225–226 |
| 12 | " | 1 | " | 3-methylbenzothienyl | " | 93 | powder |
| 13 | " | 1 | " | 2-quinolyl | ethyl | 96 | " |
| 14 | 2-methoxyphenyl | 1 | t-butyl | " | isopropyl | 67 | >300 |
| 15 | 2-methoxybenzyl | 1 | ethyl | 3-quinolyl | " | 95 | powder |
| 16 | hydrogen atom | 1 | " | 2-quinolyl | " | 90 | >300 |

Example 18

Production of t-Butyl [2,4(1H,3H)-dioxo-6-carboxy-7-isopropyl-1-(2-methoxbenzyl)-5-[2-(4-quinolonyl)]pyrido[2,3-d]pyrimidine]-3-acetate (Chemical Formula 32)

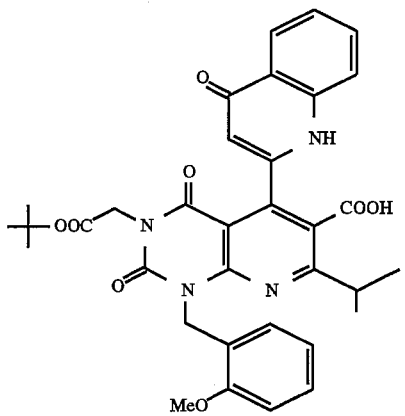

(32)

The compound (500 mg, 0.82 mmol.) obtained in Example 16 was dissolved in dichloromethane (20 ml). To the solution was added thionyl chloride (0.60 ml, 8.20 mmol), and the mixture was heated for 30 minutes under reflux. The reaction mixture was cooled and concentrated. The residue was dissolved in dimethylacetamide (40 ml) and stirred with 2N aqueous solution of potassium carbonate for 22 hours at 90° C. After cooling, the reaction mixture was poured into ice-water and was adjusted to pH ranging from 1 to 2 with 1N HCl, which was subjected to extraction with ethyl acetate (150 ml). The organic layer was washed by a saturated aqueous solution of sodium chloride, and dried, then the solvent was distilled off under reduced pressure. The residue was purified by means of a silica gel column chromatography to give 190 mg (yield 37%) of pale brown powder. The powder thus obtained were recrystallized from mixed solvent of iso-propanol and isopropyl ether to give 40 mg (yield 8%) of pale brown powdery crystals, m.p. more than 300° C. The elemental analysis values were shown in Table 24. The NMR spectrum and IR spectrum of thus obtained compound are as follows.

$^1$H-NMR (200 MHz, DMSO-$d_6$) δ ppm: 0.97(3H,d), 1.07(3H,d), 1.33(9H,s), 3.46(1H,m), 3.90(3H,s), 4.48(2H,s), 5.52(2H,q), 5.92(1H,s), 6.80(2H,s), 7.04(1H,d), 7.22(1H, td), 7.28(1H,t), 7.44(1H,d), 7.58(1H,td), 8.10(1H,d), 11.81 (1H,s).

IR (KBr): 3452, 2974, 1717, 1673, 1638, 1601, 1570, 1510, 1473, cm$^{-1}$.

TABLE 24

Elemental Analysis for $C_{34}H_{34}N_4O_7 \cdot 3.0HCl \cdot 2.0H_2O$

|  | C (%) | H (%) | N (%) |
|---|---|---|---|
| Calcd. | 52.89 | 5.35 | 7.26 |
| Found | 52.71 | 5.16 | 7.22 |

Example 19

Using compounds reffered to in Example 17 and others, the method described in Example 18 was repeated. Compounds thus obtained (Chemicl Formula 33) are listed in Table 25.

TABLE 25

(33)

| Ex. 19 Cpd. No. | 1-substit. ($R^1$) | n | ($R^2$) | 7-subs tit. ($R^5$) | Yield (%) | m.p. (°C.) |
|---|---|---|---|---|---|---|
| 1 | 2-methoxy-benzylyl | 1 | T-butyl | methyl | 33 | >300 |
| 2 | 2-methoxy-benzylyl | 1 | ethyl | iso-propyl | 72 | >300 |
| 3 | 2-methoxy-benzylyl | 3 | " | iso-propyl | 25 | 264–266 |
| 4 | 2-methoxy-benzylyl | 1 | t-butyl | phenyl | 51 | >300 |
| 5 | 2,4-dimeth oxybenzyl | 1 | ethyl | iso-propyl | 14 | >300 |
| 6 | 2,4-dimeth oxybenzyl | 1 | t-butyl | iso-propyl | 20 | 228–230 |
| 7 | methyl | 1 | ethyl | iso-propyl | 81 | 259–261 |
| 8 | 3-methoxy-benzyl | 1 | " | methyl | 56 | 280–283 |
| 9 | 2-methoxy-benzyl | 1 | t-butyl | 3,4-me thylen edioxy phenyl | 50 | >300 |
| 10 | 2-methoxy-benzyl | 1 | ethyl | normal propyl | 41 | 149–150 |
| 11 | 2-methoxy-benzyl | 1 | " | iso-butyl | 63 | 283–285 |
| 12 | 2-methoxy-benzyl | 1 | " | ethyl | 19 | >300 |
| 13 | 2-methoxy-phenyl | 1 | " | iso-propyl | 60 | >300 |

Example 20

Production of 2,4(1H,3H)-dioxo-6-carboxy-7-isopropyl-1-(2-methoxybenzyl)-5-[2-(4-quinolonyl)pyrido[2,3-d]pyrimidine-3-acetic Acid (Chemical Formula 34)

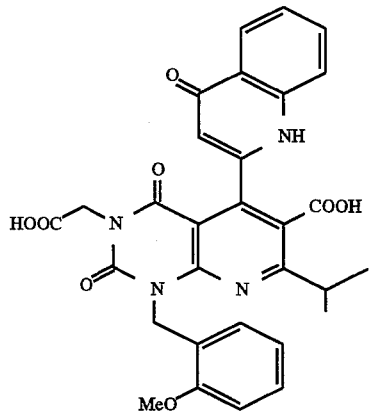
(34)

The compound (Compound No. 2: 0.19 g, 0.32 mmol.) obtained in Example 19 was dissolved in the mixture of methanol (2.0 ml) and tetrahydrofuran (2.0 ml), to which was added a 1N aqueous solution of sodium hydroxide (0.64 ml, 1.3 mmol), and the mixture was stirred for 5 hours at room temperature. The reaction mixture was adjusted to pH ranging from 1 to 2 with 1N HCl, which was subjected to extraction with mixed solvent of ethyl acetate and tetrahydrofuran.

The organic layer was washed by a saturated aqueous solution of sodium chloride, and dried, then the solvent was distilled off under reduced pressure. The residue was recrystallized from mixed solvent of methanol and isopropyl ether to give 0.08 g (yield 44%) of colorless powdery crystals, m.p. over 300° C. Elemental analysis of the product is shown in Table 26. The NMR spectrum and IR spectrum of the compound were as follows.

$^1$H-NMR (200 MHz, DMSO-$d_6$) δ ppm: 1.01(3H,d), 1.13(3H,d), 3.18(1H,m), 3.90(3H,s), 4.55(2H,q), 5.53(2H,q), 5.92(1H,s), 6.81–6.94(2H,m), 7.04(1H,d), 7.24(1H,t), 7.35(1H,t), 7.47(1H,d), 7.65(1H,t), 8.12(1H,d), 11.90(1H,s), 13.0(1H,brs).

IR (KBr): 3444, 2974, 1719, 1676, 1574, 1493 cm$^{-1}$.

TABLE 26

Elemental Analysis for $C_{30}H_{26}N_4O_7 \cdot 0.5H_2O$

|  | C (%) | H (%) | N (%) |
|---|---|---|---|
| Calcd. | 62.17 | 4.70 | 9.67 |
| Found | 62.13 | 4.70 | 9.41 |

Example 21

Using compounds reffered to in Example 19 and others, the method described in Example 20 was repeated. Compounds thus obtained (Chemicl Formula 35) are listed in Table 27.

TABLE 27

(35)

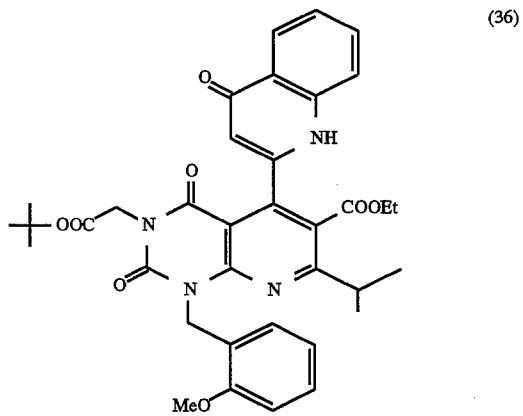

| Ex. 21 Cpd. No. | 1-substit. (R$^1$) | 7-substit. (R$^5$) | Yield (%) | m.p. (°C.) |
|---|---|---|---|---|
| 1 | 2-methoxybenzyl | methyl | 65 | >300 |
| 2 | 2-methoxybenzyl | phenyl | 58 | >300 |
| 3 | 2-methoxybenzyl | methyl | 70 | >300 |
| 4 | methyl | iso-propyl | 57 | >300 |
| 5 | 2,4-dimethoxybenzyl | " | 100 | 274–276 |
| 6 | 2-methoxybenzyl | normal propyl | 73 | >300 |
| 7 | 2-methoxybenzyl | iso-butyl | 90 | >300 |
| 8 | 2-methoxybenzyl | ethyl | 50 | >300 |
| 9 | 2-methylthiobenzyl | iso-propyl | 53 | >300 |
| 10 | 2,3-dimethoxybenzyl | " | 75 | >300 |
| 11 | 2,3,4-trimethoxybenzyl | " | 73 | >300 |

Example 22

Production of t-Butyl [2,4(1H,3H)-dioxo-6-ethoxycarbonyl-7-isopropyl-1-(2-methoxybenzyl)-5-[2-(4-quinolonyl)]pyrido[2,3-d]pyrimidine]-3-acetate (Chemical Formula 36)

(36)

The compound (0.35 g, 0.56 mmol.) obtained in Example 18 was stirred with ethyl iodide (0.10 g, 0.91 mmol) in dimethylformamide (5.0 ml) for one hour at room temperature. The reaction mixture was adjusted to pH ranging from 1 to 2 with 1N HCl, and was subjected to distribution in ethyl acetate and water. The organic layer was dried, then the solvent was distilled off under reduced pressure. The residue was purified by means of a silica gel column chromatography to give 0.18 g (yield 49%) of a pale brown amorphous product. The elemental analysis values of the compound thus obtained were shown in Table 28. The NMR spectrum and IR spectrum of the compound are as follows.

TABLE 28

| Elemental Analysis for $C_{36}H_{38}N_4O_6 \cdot 0.75H_2O$ | | | |
|---|---|---|---|
| | C (%) | H (%) | N (%) |
| Calcd. | 64.71 | 5.96 | 8.38 |
| Found | 64.63 | 5.71 | 8.32 |

$^1$H-NMR (200 MHz, CDCl$_3$) δ ppm: 0.98(3H,t), 1.08(3H, d), 1.19(3H,d), 1.42(9H,s), 3.15(1H,m), 3.88(3H,s), 4.09 (2H,t), 4.61(2H,q), 5.64(2H,q), 6.16(1H,s), 6.79–7.01(3H, m), 7.18–7.37(3H,m), 7.59(1H,td), 8.33(1H,dd).

IR (KBr): 3450, 2978, 2936, 1721, 1682, 1638, 1605, 1574, 1510, 1460 cm$^{-1}$.

Example 23

Production of 2,4(1H,3H)-dioxo-6-ethoxycarbonyl-7-isopropyl-1-(2-methoxybenzyl)-5-[2-(4-quinolonyl)]pyrido[2,3-d]pyrimidine-3-acetic Acid (Chemical Formula 37)

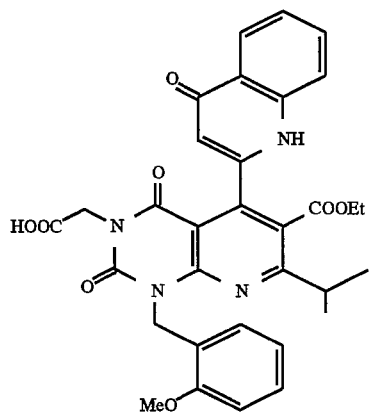

(37)

The compound (0.15 g, 0.23 mmol.) obtained in Example 22 was dissolved in dichloromethan and was stirred with trifuluoroacetic acid for 1 hour at room temperature. The reaction mixture was distilled off under reduced pressure. The residue was recrystallized from mixed solvent of isopropyl alcohol and isopropyl ether to give 0.12 g (yield 86%) of pale yellow powdery crystals, m.p. 214°–216° C. Elemental analysis of the product is shown in Table 29, The NMR spectrum and IR spectrum of the compound were as follows.

TABLE 29

| Elemental Analysis for $C_{32}H_{30}N_4O_6 \cdot 0.5H_2O$ | | | |
|---|---|---|---|
| | C (%) | H (%) | N (%) |
| Calcd. | 60.46 | 4.69 | 8.55 |
| Found | 60.14 | 4.93 | 8.80 |

$^1$H-NMR (200 MHz, DMSO-d$_6$) δ ppm: 0.79(3H,t), 0.99 (3H,d), 1.13(3H,d), 3.10(1H,m), 3.89(3H,s), 4.00(2H,t), 4.55(2H,q), 5.53(2H,q), 5.92(1H,s), 6.79–6.92(2H,m), 7.05 (1H,d), 7.24(1H,t), 7.37(1H,t), 7.49(1H,d), 7.68(1H,t), 8.13 (1H,d), 12.18(1H,br).

IR (KBr): 3444, 2972, 2936, 1719, 1680, 1603, 1574, 1492, 1462 cm$^{-1}$.

Example 24

Using compounds wherein the substituent at 3-position is —CH$_2$COO(t-C$_4$H$_9$). the method described in Example 23 was repeated. Compounds thus obtained (Chemicl Formula 38) are listed in Table 30.

TABLE 30

| Ex. 24 Cpd. No. | 1-substit. (R$^1$) | 5-substit. (QR$^3$) | 6-substit. (R$^4$) | 7-substit. (R$^5$) | Yield (%) | m.p. (°C.) |
|---|---|---|---|---|---|---|
| 1 | 2-methoxy-benzyl | 2-(4-quinolonyl) | N-ethyl-carbamoyl | isopropyl | 92 | 206–207 |
| 2 | " | " | carbamoyl | " | 46 | >300 |
| 3 | 2-methoxy-phenyl | " | carboxyl | " | 46 | >300 |
| 4 | 2-methoxy-benzyl | 2-quinolyl | ethoxycarbonyl | 3,4-methylene-dioxy-phenyl | 97 | 145–147 |
| 5 | " | " | " | phenyl | 90 | 215–217 |
| 6 | " | " | " | methyl | 50 | 112–113 |
| 7 | " | " | carboxyl | 3,4-methylene- | 43 | 202–204 |

TABLE 30-continued

![Formula 38]

| Ex. 24 Cpd. No. | 1-substit. (R¹) | 5-substit. (QR³) | 6-substit. (R⁴) | 7-substit. (R⁵) | Yield (%) | m.p. (°C.) |
|---|---|---|---|---|---|---|
| 8 | " | " | " | dioxyphenyl phenyl | 74 | 204–206 |
| 9 | " | " | " | methyl | 93 | 245–246 |
| 10 | " | 2-(4-quinolonyl) | " | " | 65 | >300 |
| 11 | " | " | " | phenyl | 58 | >300 |

Example 25

Production of Ethyl [2,4(1H,3H)-dioxo-6-isobutoxycarbonyl-7-isopropyl-1-(2-methoxybenzyl)-5-(2-quinolyl)pyrido[2,3-d]pyrimidine]-3-acetate (Chemical Formula 39)

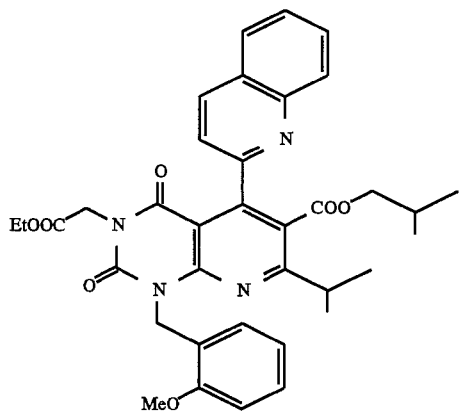

(39)

The compound (Compound No. 1: 0.26 g, 0.44 mmol.) obtained in Example 17 was dissolved in dimethylformamide and was stirred with with isobutylbromide (0.14 ml, 1.81 mmol) and potassium carbonate (0.19 g, 1.36 mmol) for 24 hours at room temperature. The reaction mixture was adjusted to pH ranging from 1 to 2 with 1N HCl, and was subjected to distribution in ethyl acetate and water. The organic layer was dried, then the solvent was distilled off under reduced pressure. The residue was purified by means of a silica gel column chromatography to give 0.21 g (yield 75%) of a colorless amorphous product. Elemental analysts of the product is shown in Table 81. The NMR spectrum and IR spectrum of the compound were as follows.

TABLE 31

| Elemental Analysis for $C_{38}H_{33}N_4O_7$ | | | |
|---|---|---|---|
| | C (%) | H (%) | N (%) |
| Calcd. | 67.70 | 6.00 | 8.77 |
| Found | 67.67 | 6.22 | 8.59 |

$^1$H-NMR (200 MHz, CDCl$_3$) δ ppm: 0.66(6H,d), 1.14 (6H,d), 1.23(3H,t), 1.55(1H,m), 3.14(1H,m), 3.53(2H,d), 3.91(3H,s), 4.14(2H,q), 4.68(2H,s), 5.69(2H,s), 6.86–7.00 (3H,m), 7.21(1H,td), 7.50(1H,d), 7.56(1H,t), 7.71(1H,td), 7.86(1H,d), 8.04(1H,d), 8.19(1H,d).

IR (KBr): 3456, 2976, 2968, 1721, 1678, 1574, 1495 cm$^{-1}$.

Example 26

Using the compounds obtained in Example 16 and 17, the method described in Example 25 was repeated. The compounds thus obtained (Chemical Formula 40) were listed in Table 32.

TABLE 32

(40)

| Ex. 26 Cpd. No. | R² | 6-substit. (R⁴) | 7-sub stit. (R⁵) | Yield (%) | m.p. (°C.) |
|---|---|---|---|---|---|
| 1 | ethyl | isopropoxy-carbonyl | iso-propyl | 25 | powder |
| 2 | " | cyclohexyl oxy-carbonyl | iso-propyl | 79 | " |
| 3 | " | cyclohexyl-met hoxy-carbonyl | iso-propyl | 73 | " |
| 4 | " | benzyloxy-carbonyl | iso-propyl | 73 | " |
| 5 | " | 2-quinolylmeth oxy-carbonyl | iso-propyl | 88 | " |
| 6 | " | carboxy-methoxy carbonyl | iso-propyl | 80 | " |
| 7 | " | methoxy-carbonyl | iso-propyl | 64 | " |
| 8 | " | ethoxycarbonyl | iso-propyl | 87 | " |

TABLE 32-continued (40)

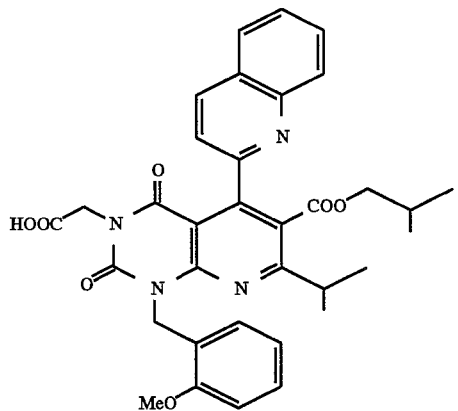

| Ex. 26 Cpd. No. | R² | 6-substit. (R⁴) | 7-substit. (R⁵) | Yield (%) | m.p. (°C.) |
|---|---|---|---|---|---|
| 9 | " | 2-cyanoethoxy-carbonyl | 3,4-methylenedioxyphenyl | 86 | " |
| 10 | t-butyl | ethoxycarbonyl | methyl | 87 | " |
| 11 | " | " | phenyl | 53 | " |
| 12 | " | " | 3,4-methylenedioxyphenyl | 86 | " |

Example 27

Production of 2,4(1H,3H)-dioxo-6-isobutoxycarbonyl-7-isopropyl-1-(2-methoxybenzyl)-5-(2-quinolyl)pyrido[2,3-d]pyrimidine-3-acetic Acid (Chemical Formula 41)

(41)

The compound (0.19 g, 0.30 mmol.) obtained in Example 25 was dissolved in the mixed solvent of methanol (2.0 ml) and tetrahydrofuran (2.0 ml), to which was added a 2N aqueous solution of sodium hydroxide (0.60 ml, 1.2 mmol), and the mixture was stirred for 110 minutes at room temperature. The reaction mixture was adjusted to pH ranging from 1 to 2 with 1N HCl, which was subjected to distribution to ethyl acetate and water. The organic layer was washed by a saturated aqueous solution of sodium chloride, and dried, then the solvent was distilled off under reduced pressure. The residue was recrystallized from mixed solvent of isopropanol and hexane to give 0.11 g (yield 61%) of colorless powdery crystals, m.p. 224°–225° C. Elemental analysis of the product is shown in Table 33. The NMR spectrum and IR spectrum of the compound were as follows.

$^1$H-NMR (200 MHz, DMSO-$d_6$) δ ppm: 0.57(6H, d), 1.03(6H,d), 1.38(1H,m), 3.10(1H,m), 3.50(2H,br), 3.90(3H, s), 4.50(2H,s), 5.54(2H,s), 6.83(1H,t), 6.94(1H,d), 7.06(1H, d), 7.24(1H,t), 7.56(1H,d), 7.65(1H,t), 7.78(1H,t), 7.90(1H, d), 8.02(1H,d), 8.34(1H,d).

IR (KBr): 3480, 2970, 1717, 1665, 1574, 1466 cm$^{-1}$.

TABLE 33

Elemental Analysis for $C_{34}H_{34}N_4O_7 \cdot 0.5C_3H_8O \cdot 0.5H_2O$

| | C (%) | H (%) | N (%) |
|---|---|---|---|
| Calcd. | 65.17 | 6.09 | 8.56 |
| Found | 65.04 | 6.21 | 8.54 |

Example 28

Using the compounds obtained in Example 2 (Comp. No. 27,28) and Example 26, the method described in Example 27 was repeated. The compounds thus obtained (Chemical Formula 42) were listed in Table 34.

TABLE 34

(42)

| Ex. 28 Cpd. No. | 5-substit. (QR³) | 6-substit. (R⁴) | Yield (%) | m.p. (°C.) |
|---|---|---|---|---|
| 1 | 2-quinolyl | isopropoxy-carbonyl | 61 | 224–225 |
| 2 | " | cyclohexyl-oxy-carbony | 75 | 218–220 |
| 3 | " | cyclohexyl-methoxy-carbonyl | 32 | 116–118 |
| 4 | " | benzyloxy-carbonyl | 95 | 108–110 |
| 5 | " | 2-quinolylmethoxy-carbonyl | 16 | 133–135 |
| 6 | " | carboxymethoxy-carbonyl | 93 | powder |
| 7 | " | methoxy-carbonyl | 80 | >300 |
| 8 | " | ethoxycarbonyl | 86 | powder |
| 9 | " | " | 48 | 155–157 |
| 10 | 3,4-dimethoxyphenyl | " | 79 | 135–136 |

Example 29

Production of 2,4(1H,3H)-dioxo-6-cyanoethoxycarbonyl-7-isopropyl-1-(2-methoxybenzyl)-5-(2-quinolyl)pyrido[2,3-d]pyrimidine-3-acetic Acid (Chemical Formula 43)

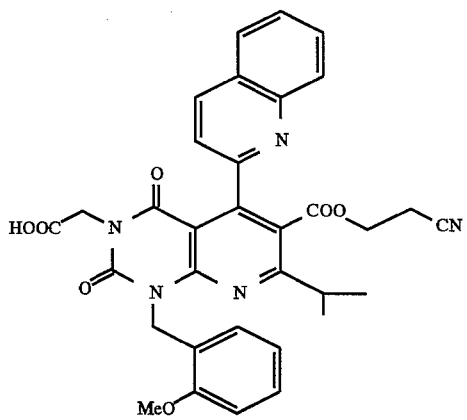

(43)

The compound (0.30 g, 0.45 mmol.) obtained in Example 3 was dissolved in dichloromethan (3.0 ml) and was stirred with trifuluoroacetic acid (1 ml) for 4.5 hours at room temperature. The reaction mixture was distilled off under reduced pressure. The residue was purified by means of a silica gel column chromatography to give 0.31 g of a pale yellow powdery crystals. The crystals were recrystallized from mixed solvent of ethylacetate and hexane to give 0.21 g (yield 78%) of colorless powdery crystals, m.p. 115°–116° C. Elemental analysis of the product is shown in Table 35. The NMR spectrum and IR spectrum of the compound were as follows.

TABLE 35

Elemental Analysis for $C_{33}H_{29}N_5O_7 \cdot 0.5H_2O \cdot 0.5CF_3COOH$

|  | C (%) | H (%) | N (%) |
|---|---|---|---|
| Calcd. | 60.62 | 4.56 | 10.40 |
| Found | 60.86 | 4.86 | 9.93 |

$^1$H-NMR (200 MHz, DMSO-$d_6$) δ ppm: 1.06(6H,d), 2.50(2H,t), 3.78(2H,t), 3.13(1H,m), 3.91(3H,s), 4.50(2H,s), 5.55(2H,s), 6.84(1H,t), 6.95(1H,d), 7.05(1H,d), 7.21(1H,t), 7.59(1H,d), 7.67(1H,t), 7.79(1H,t), 7.97(1H,d), 8.04(1H,d), 8.35(1H,d).

IR (KBr): 3438, 2972, 2270, 1719, 1676, 1574, 1495, 1466 cm$^{-1}$.

Example 30

Using the compounds obtained in Example 4 (Compd. No. 1) and Example 26 (Compd. Nos. 10–12), the method described in Example 29 was repeated. The compounds thus obtained (Chemical Formula 44) were listed in Table 36.

TABLE 36

(44)

| Ex. 30 Cpd. No. | 5-substit. (QR$^3$) | 6-substit. (R$^4$) | 7-substit. (R$^5$) | Yield (%) | m.p. (°C.) |
|---|---|---|---|---|---|
| 1 | 4-tolyl | 2-cyanoethoxy carbonyl | iso-propyl | 73 | 213–215 |
| 2 | 2-quinolyl | ethoxycarbonyl | methyl | 50 | 112–113 |
| 3 | 2-quinolyl | cyclohexyl-methoxy-carbonyl | phenyl | 90 | 215–217 |
| 4 | 2-quinolyl | benzyloxy-carbonyl | 3,4-methylendioxyphenyl | 97 | 145–147 |

Example 31

Production of Ethyl [2,4(1H,3H)-dioxo-6-carboxy-7-isopropyl-1-(2-methylthiobenzyl)-5-[2-(4-quinolonyl)]pyrido[2,3-d]pyrimidine]-3-acetate (Chemical Formula 45)

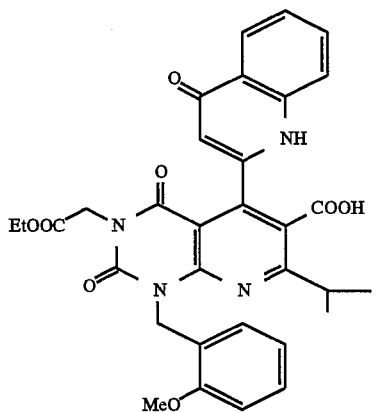

(45)

The acetonitrile solution (15 ml) containing the compound (150 mg, 0.25 mmol.) obtained in Reference Example 13, 2N aqueous solution of potassium carbonate (1.25 ml, 2.50 mmol) and water (1.5 ml) was stirred for 30 minutes at a temperature of 50° C. To the reaction mixture was added 1N HCl (5 ml), which was subjected to distribution to ethyl acetate and saturated aqueous solution of sodium chloride.

The organic layer was dried with MgSO$_4$, and then the solvent was distilled off under reduced pressure. The residue was recrystallized from isopropanol to give 83 mg (yield 54%) of colorless powdery product, m.p. 167°–170° C. Elemental analysis of the product is shown in Table 37. The NMR spectrum, IR spectrum and MS spectrum of the compound were as follows.

$^1$H-NMR (500 MHz, DMSO-$d_6$) δ ppm: 1.03(6H,d), 1.15(3H,t), 2.59(3H,s), 3.16–3.24(1H,m), 4.11(2H,q), 4.59(1H,d) 4.69(1H,d), 5.53(2H,s), 6.29(1H,s), 6.86(1H,d), 7.09(1H,t) 7.29(1H,t), 7.41(1H,d), 7.50(1H,t), 7.63(1H,d), 7.79(1H,t), 8.21(1H,d), 12.90(1H,bds).

IR (KBr): 3428, 1721, 1678, 1574, 1491, 1369 cm$^{-1}$.
FAB-MS m/z: 615.1(MH+).

TABLE 37

Elemental Analysis for $C_{32}H_{30}N_4O_7S \cdot 0.5CHCl_3$

|  | C (%) | H (%) | N (%) |
|---|---|---|---|
| Calcd. | 57.88 | 4.56 | 8.31 |
| Found | 57.73 | 4.51 | 8.42 |

Example 32

Using the compounds obtained in Reference Example 14 the method described in Example 31 was repeated. The compounds thus obtained (Chemical Formula 46) were listed in Table 38.

TABLE 38

(46)

[Structure diagram]

| Ex. 32 Cpd. No. | 1-substit. (R$^4$) | 7-sub stit. (R$^5$) | Yield (%) | m.p. (°C.) |
|---|---|---|---|---|
| 1 | 2,3-dimethoxy-benzyl | iso-propyl | 67 | 245–250 |
| 2 | 2,3,4-trimethoxy-benzyl | iso-propyl | 68 | 158–161 |

Example 33

Production of t-Butyl [2,4(1H,3H)-dioxo-6-carbamoyl-7-isopropyl-1-(2-methoxbenzyl)-5-[2-(4-quinolonyl)]pyrido[2,3-d]pyrimidine]-3-acetate (Chemical Formula 47)

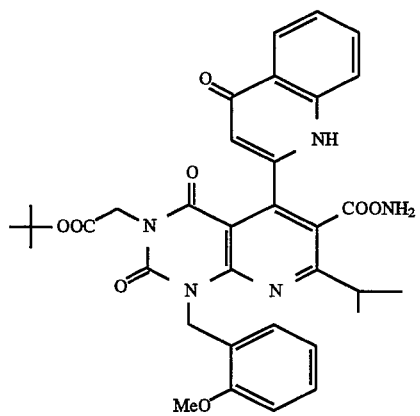

(47)

The compound (500 mg, 0.82 mmol.) obtained in Example 16 was dissolved in dichloromethane (20 ml). To the solution was added thionyl chloride (0.60 ml, 8.20 mmol), and the mixture was heated for 30 minutes under reflux. The reaction mixture was cooled and concentrated to dryness.

The residue was suspended in a mixed solvent of tetrahydrofuran (5 ml) and dimethylacetamide (20 ml), and then was stirred with 25% aqueous ammonia (10 ml) for 15 minutes at room temperature. The reaction mixture was poured into ice-water and was adjusted to pH ranging from 1 to 2 with 1N HCl, which was then subjected to extraction with ethyl acetate (150 ml). The organic layer was washed with a saturated aqueous solution of sodium chloride, and dried, then the solvent was distilled off under reduced pressure. The residue was purified by means of a silica gel column chromatography to give 310 mg (yield 61%) of colorless powder. The powder thus obtained were recrystallized from mixed solvent of iso-propanol and isopropyl ether to give 170 mg (yield 33%) of colorless powdery crystals, m.p. more than 300° C. The elemental analysis values were shown in Table 39. The NMR spectrum and IR spectrum of thus obtained compound are as follows.

$^1$H-NMR (200 MHz, DMSO-d$_6$) δ ppm: 1.01(3H,d), 1.13(3H,d), 1.37(9H,s), 3.20(1H,m), 3.90(3H,s), 4.53(2H,s), 5.53(2H,s), 6.06(1H,s), 6.83–6.89(2H,m), 7.06(1H,d), 7.23(1H,td), 7.32(1H,t), 7.44(1H,d), 7.63(1H,t), 7.75(1H,br), 7.95(1H,br), 8.11(1H,d), 11.82(1H,br).

IR (KBr): 3428, 1721, 1678, 1638, 1605, 1572, 1512, 1475 cm$^{-1}$.

TABLE 39

Elemental Analysis for $C_{36}H_{38}N_6O_7 \cdot H_2O$

|  | C (%) | H (%) | N (%) |
|---|---|---|---|
| Calcd. | 63.44 | 5.79 | 10.88 |
| Found | 63.41 | 5.80 | 10.93 |

Example 34

Using the compounds obtained in Example 16, the method described in Example 33 was repeated, while employing 70% aqueous solution of ethylamine in place of 25% aqueous ammonia. The compound thus obtained (Chemical Formula 48) was listed in Table 40.

TABLE 40

(48)

[Structure diagram]

| Ex. 34 Cpd. No. | (R$^2$) | 5-substit. (QR$^3$) | 6-substit. (R$^4$) | Yield (%) | m.p. (°C.) |
|---|---|---|---|---|---|
| 1 | t-butyl | 2-(4-quinolonyl) | N-ethyl-carbamoyl | 20 | 172–173 |

Example 35

Production of t-Butyl [2,4(1H,3H)-dioxo-6-carboxy-7-isopropyl-1-(2-methoxbenzyl)-5-(quinoline-1-oxide-2-yl)pyrido[2,3-d]pyrimidine]-3-acetate (Chemical Formula 49)

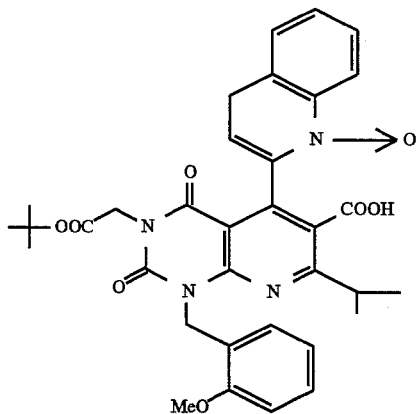

(49)

The compound (300 mg, 0.49 mmol.) obtained in Example 16 was dissolved in dichloromethane (20 ml). To the solution was added m-chlorobenzoyl hydroperoxide (0.25 g), and the mixture was stirred for 21 hours at room temperature. To the reaction mixture was added isopropyl ether (80 ml) to give 200 mg (yield 65%) of colorless powdery crystals, m.p. 176°–178° C. The elemental analysis values were shown in Table 41. The NMR spectrum and IR spectrum of thus obtained compound are as follows.

$^1$H-NMR (200 MHz, DMSO-d$^6$) δ ppm: 1.07(6H,d), 1.34(9H,s), 3.33(1H,m), 3.90(3H,s), 4.44(2H,s), 5.53(2H,s), 6.79–6.90(2H,m), 7.05(1H,d), 7.24(1H, td), 7.43(1H,d), 7.80–7.97(3H,m), 8.12(1H,d), 8.49(1H,d).

IR (KBr): 3445, 2974, 2372, 1719, 1673, 1572, 1460 cm$^{-1}$.

TABLE 41

Elemental Analysis for $C_{34}H_{34}N_4O_8 \cdot .25H_2O$

|  | C (%) | H (%) | N (%) |
|---|---|---|---|
| Calcd. | 62.91 | 5.67 | 8.63 |
| Found | 62.91 | 5.42 | 8.24 |

Example 36

Using the compounds obtained in Example 17 the (Comp. No. 15) method described in Example 35 was repeated. The compound thus obtained (Chemical Formula 50) was listed in Table 42.

TABLE 42

(50)

(Structure showing R$^2$OOC-CH$_2$-N, quinoline with QR$^3$ and COOH substituents, isopropyl group, and 2-methoxybenzyl group)

| Ex. 36 Cpd. No. | (R$^2$) | 5-substit. (QR$^3$) | Yield (%) | m.p. (°C.) |
|---|---|---|---|---|
| 1 | ethyl | quinoline-1-oxide-3-yl | 12 | powder |

Example 37

Formulation of Tablets Containing the Compound of This Invention as Effective Component (1)

Using 100 mg of the compound of compound number 2 in Example 19 of the present invention, 165 mg of lactose, 25 mg of corn starch, 4 mg of polyvinyl alcohol, 5 mg of avicel and 1 mg of magnesium stearate, tablets are prepared by a conventional process.

Example 38

Formulation of Tablets Containing the Compound of This Invention as Effective Component (2)

Using 100 mg of the compound of Example 10 of the present invention, 165 mg of lactose, 25 mg of corn starch, 4 mg of polyvinyl alcohol, 5 mg of avicel and 1 mg of magnesium stearate, tablets are prepared by a conventional process.

Example 39

Formulation of Tablets Containing the Compound of This Invention as Effective Component (3)

Using 100 mg of the compound of Example 12 of the present invention, 165 mg of lactose, 25 mg of corn starch, 4 mg of polyvinyl alcohol, 5 mg of avicel and 1 mg of magnesium stearate, tablets are prepared by a conventional process.

Example 40

Formulation of Tablets Containing the Compound of This Invention as Effective Component (4)

Using 100 mg of the compound of Example 20 of the present invention, 165 mg of lactose, 25 mg of corn starch, 4 mg of polyvinyl alcohol, 5 mg of avicel and 1 mg of magnesium stearate, tablets are prepared by a conventional process.

Example 41

Formulation of Tablets Containing the Compound of This Invention as Effective Component (5)

Using 100 mg of compound number 9 obtained in Example 21 of the present invention, 165 mg of lactose, 25 mg of corn starch, 4 mg of polyvinyl alcohol, 5 mg of avicel and 1 mg of magnesium stearate, tablets are prepared by a conventional process.

Example 42

Formulation of Injection Containing the Compound of This Invention as Effective Component (1)

In 15 mg of a 1M aqueous solution of sodium hydroxide is dissolved 5 g of the compound of compound number 2 obtained in Example 19 of the present invention. The solution is adjusted to pH 7.6 with a 0.1M HCl, to which is added water for injection to make the whole volume 100 ml. This solution is subjected to sterilizing filtration using 0.22 µm membrane filter, which is distributed into sterilized vials in 2 ml each portion, followed by conventional lyophilization to afford lyophilized injections in a form of 100 mg/vial.

Example 43

Formulation of Injection Containing the Compound of This Invention as Effective Component (2)

In 15 mg of a 1M aqueous solution of sodium hydroxide is dissolved 5 g of the compound of Example 10 of the present invention. The solution is adjusted to pH 7.6 with a 0.1M HCl, to which is added water for injection to make the whole volume 100 ml. This solution is subjected to sterilizing filtration using 0.22 µm membrane filter, which is distributed into sterilized vials in 2 ml each portion, followed by conventional lyophilization to afford lyophilized injections in a form of 100 mg/vial.

Example 44

Formulation of Injection Containing the Compound of This Invention as Effective Component (3)

In 15 mg of a 1M aqueous solution of sodium hydroxide is dissolved 5 g of the compound of Example 12 of the present invention. The solution is adjusted to pH 7.6 with a 0.1M HCl, to which is added water for injection to make the whole volume 100 ml. This solution is subjected to sterilizing filtration using 0.22 µm membrane filter, which is distributed into sterilized vials in 2 ml each portion, followed by conventional lyophilization to afford lyophilized injections in a form of 100 mg/vial.

Example 45

Formulation of Injection Containing the Compound of This Invention as Effective Component (4)

In 15 mg of a 1M aqueous solution of sodium hydroxide is dissolved 5 g of the compound of Example 20 of the present invention. The solution is adjusted to pH 7.6 with a 0.1M HCl, to which is added water for injection to make the whole volume 100 ml. This solution is subjected to sterilizing filtration using 0.22 µm membrane filter, which is distributed into sterilized vials in 2 ml each portion, followed by conventional lyophilization to afford lyophilized injections in a form of 100 mg/vial.

Example 46

Formulation of Injection Containing the Compound of This Invention as Effective Component (5)

In 15 mg of a 1M aqueous solution of sodium hydroxide is dissolved 5 g of the compound of compound number 9 obtained in Example 21 of the present invention. The solution is adjusted to pH 7.6 with a 0.1M HCl, to which is added water for injection to make the whole volume 100 ml. This solution is subjected to sterilizing filtration using 0.22 µm membrane filter, which is distributed into sterilized vials in 2 ml each portion, followed by conventional lyophilization to afford lyophilized injections in a form of 100 mg/vial.

[Pharmacological Experiment—1]

Endothelin Receptor-Assay

Endothelin-A receptors was prepared by diluting a fraction of porcine cardiac ventricular muscle membrane with an assay buffer [20 mM Tris-HCl, 2 mM EGTA (ethyleneglycol bis(2-aminoethylether) tetra acetic acid), 5 mM magnesium acetate, 0.1% BSA (bovine serum albumin), 0.03% $NAN_3$, 0.5 mM PMSF (phenyl methyl sulfonyl fluoride), 20 µg/ml leupeptin, 4 µg/ml E-64 (products of the Peptide Institute), 1 µg/ml pepstatin, (pH 7.2)] to make a solution of the fraction of porcine cardiac ventricular membrane (12 µg/ml).

Endothelin-B receptor was prepared by diluting a fraction of bovine cerebral membrane with the same assay buffer as mentioned above to make a solution having a concentration of 180 µg/ml.

To 100 µl of each portion was added 5 nM [$^{125}$I] endothelin-1 (2 µl). A dimethylsulfoxide solution (3 µl) of the sample was added thereto and incubated at 25° C. for 60 minutes.

And, to determine the maximum binding amount ($B_0$) and non-specific binding amount (NSB), lots to which a dimethyl sulfoxide solution (3 µl) or a dimethyl sulfoxide solution (3 µl) containing endothelin-1 ($10^{-5}$M) was added were also incubated.

These lots were supplemented with 0.05% CHAPS (3-[(3-chloroamidopropyl)dimethylammonio]-1-propanesulfonate)-assay buffer (1.5 ml), subjected to filtration through a glass fiber filter GF/F (trade name; product of Wattman Ltd. (England)), and then washed with the same buffer (1.5 ml).

Radioactivity on the filter was counted in a gamma-counter to determine the Percent Maximum Binding (PMB) in accordance with the following calculation formula.

The concentration causing PMB=50% was determined as $IC_{50}$ value. $IC_{50}$ values of some of the compounds of this invention, synthesized in the above-mentioned examples, are shown in Table 43.

$$PMB=[(B-NSB)/(B_0-NSB)]\times 100$$

TABLE 43

| | $IC_{50}$ value: µM | |
|---|---|---|
| Compound No. | Endothelin-A Receptor (porcine) | Endothelin-B Receptor (bovine) |
| Cpd. of Ex. 10 | 11 | 64 |
| Cpd. of Ex. 12 | 18 | 130 |

[Pharmacological Experiment—2]

Endothelin Receptor-Assay

Endothelin (ET) receptors were prepared by diluting fractions of insect cell (Sf9) membrane having human endothelin-A (ETA) receptors or human endothelin-B (ETB)

receptors appeared, with an assay buffer [20 mM Tris-HCl, 2 mM EGTA (ethyleneglycol bis(2-aminoethylether) tetra acetic acid), 5 mM magnesium acetate, 0.1% BSA (bovine serum albumin), 0.03% $NAN_3$, 0.5 mM PMS F (phenyl methyl sulfonyl fluoride), 20 µg/ml leupeptin, 4 µg/ml E-64 (products of the Peptide Institute), 1 µg/ml pepstatin, (pH 7.2)] respectively in a concentration of 1.4 µg/ml in the former case and 0.7 µg/ml in the latter case.

To 100 µl of each portion was added 5 nM [$^{125}$I] endothelin-1 (2 µl). A dimethylsulfoxide solution (3 µl) of the sample was added thereto and incubated at 25° C. for 60 minutes.

And, to determine the maximum binding amount ($B_0$) and non-specific binding amount (NSB), lots to which a dimethyl sulfoxide solution (3 µl) or a dimethyl sulfoxide solution (3 µl) containing endothelin-1 ($10^{-5}$M) had been added, were also incubated.

These lots were supplemented with 0.05% CHAPS (3-[(3-chloroamidopropyl)dimethylammonio]-1-propanesulfonate)-assay buffer (1.5 ml), subjected to filtration through a glass fiber filter GF/F (trade name; product of Wattman Ltd. (England)), and then washed with the same buffer (1.5 ml).

Radioactivity on the filter was counted in a gamma-counter to determine the Percent Maximum Binding (PMB) in accordance with the aforesaid calculation formula. The concentration causing PMB=50% was determined as $IC_{50}$ value. $IC_{50}$ values of some of the compounds of this invention, synthesized in the above-mentioned examples, are shown in Table 44.

TABLE 44

| Compound No. | | $IC_{50}$ value: µM | |
|---|---|---|---|
| | | Endothelin-A Receptor | Endothelin-B Receptor |
| Example No. | Compound No. | (human) | (human) |
| 10 | | 11 | — |
| 12 | | 22 | — |
| 14 | | 3.7 | 67 |
| 15 | 4 | 0.89 | 95 |
| 16 | | 1.6 | 69 |
| 17 | 1 | 0.71 | 19 |
| 18 | | 0.15 | 69 |
| 19 | 2 | 0.07 | 65 |
| 19 | 5 | 0.98 | 23 |
| 20 | | 0.12 | 14 |
| 21 | 9 | 0.056 | 14 |
| 23 | | 0.92 | 4.3 |
| 27 | | 4.5 | 47 |
| 28 | 8 | 1.1 | 76 |
| 29 | | 0.57 | 95 |
| 31 | | 0.12 | 88 |

According to the result shown in the table 43 and 44, it has been proved that the compound [A] or its salt of this invention have excellent endothelin receptor antagonistic action to both endothelin-A receptor and endothelin-B receptor.

The compounds of this invention have an endothelin receptor antagonistic action, which are effective as prophylactic and therapeutic agents against acute renal insufficiency, myocardial infarction, hypertension, cerebral infarction, angina pectoris, arteriosclerosis, hepatopathy, pulmonary hypertension, bronchial asthma, organohypofunction occuring during operation or transplantation of organs.

It is apparent that various modifications may be made in the foumulations and application of the novel compound of this invention, without departing from the invention concept herein, as defined in the following claims.

We claim:
1. A pyrido[2,3-d]pyrimidine derivative represented by the formula (A"):

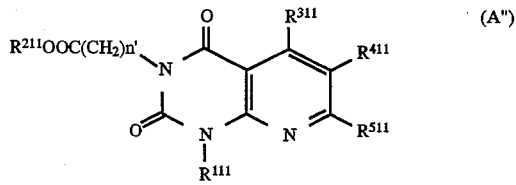

wherein n' denotes an integer of 1 to 3;
$R^{111}$ is a hydrogen atom; a $C_{1-6}$ alkyl group; or a phenyl-$C_{1-3}$ alkyl group optionally substituted by at least one member selected from the group consisting of a $C_{1-6}$ alkoxy group and a $C_{1-6}$ alkylthio group;
$R^{211}$ is a hydrogen atom or a $C_{1-6}$ alkyl group;
$R^{311}$ is (1) a phenyl group or naphthyl group optionally substituted by at least one member selected from the group consisting of a $C_{1-6}$ alkyl group, a $C_{3-7}$ cycloalkyl group, a $C_{1-6}$ alkoxy group, a halogen atom, nitro group, cyano group and phenyl group; or (2) a pyridyl group, quinolyl group, quinolonyl group or thienyl group optionally substituted by at least one member selected from the group consisting of a $C_{1-6}$ alkyl group, a $C_{1-6}$ alkoxy group, and hydroxyl group;
$R^{411}$ is —$COOR^{611}$ wherein $R^{611}$ is (1) a hydrogen atom; (2) a $C_{1-6}$ alkyl group optionally substituted by a carboxyl group, a cyano group or a quinolyl group; (3) $C_{3-7}$ cycloalkyl group; or (4) $C_{7-15}$ aralkyl group or $R^{411}$ is —$CONR^{711}R^{811}$ wherein $R^{711}$ and $R^{811}$ independently are a hydrogen atom or $C_{1-6}$ alkyl group; and
$R^{511}$ is (1) a hydrogen atom; (2) a $C_{1-6}$ alkyl group; or (3) a phenyl group optionally substituted by a $C_{1-3}$ alkylenedioxy group;
or a salt thereof.

2. 2,4(1H,3H)-Dioxo-6-ethoxycarbonyl-7-isopropyl-1-(2-methoxybenzyl)-5-(4-tolyl)pyrido[2,3-d]pyrimidine-3-acetic acid or its salt.

3. 2,4(1H,3H)-Dioxo-6-ethoxycarbonyl-7-methyl-1-(2-methoxybenzyl)-5-(4-methoxyphenyl)pyrido[2,3-d]pyrimidine-3-acetic acid or its salt.

4. Ethyl[2,4(1H,3H)-Dioxo-6-carboxy-7-isopropyl-1-(2-methoxybenzyl)-5-[2-(4-quinolonyl)]pyrido[2,3-d]pyrimidine]-3-acetate or its salt.

5. 2,4(1H,3H)-Dioxo-6-carboxy-7-isopropyl-1-(2-methoxybenzyl)-5-[2-(4-quinolonyl)]pyrido[2,3-d]pyrimidine-3-acetic acid or its salt.

6. 2,4(1H,3H)-Dioxo-6-carboxy-7-isopropyl-1-(2-methylthiobenzyl)-5-[2-(4-quinolonyl)]pyrido[2,3-d]pyrimidine-3-acetic acid or its salt.

7. A compound selected from the group consisting of
2,4(1H,3H)-dioxo-6-carboxy-7-isopropyl-1-(2-methoxybenzyl)-5-(2-quinolyl)pyrido [2,3-d]pyrimidine-3-acetic acid,
2,4(1H,3H)-dioxo-6-carboxy-7-isopropyl-1-(2,4-dimethoxybenzyl)-5-(2-quinolyl)pyrido [2,3-d]pyrimidine-3-acetic acid,
t-butyl[2,4(1H,3H)-dioxo-6-carboxy-7-isopropyl-1-(2-methoxybenzyl)-5-(2-quinolylpyrido[2,3-d]pyrimidine]-3-acetate,
ethyl[2,4(1H,3H)-dioxo-6-carboxy-7-isopropyl-1-(2-methoxybenzyl)-5-(2-quinolylpyrido[2,3-d]pyrimidine]-3-acetate, t-butyl [2,4(1H,3H)-dioxo-6-carboxy-7-isopropyl-1-(2-methoxybenzyl)-5-[2-(4-quinolonyl)]pyrido[2,3-d]pyrimidine]-3-acetate, ethyl[2,4(1H,3H)-dioxo-6-carboxy-7-isopropyl-1-(2,4-dimethoxybenzyl)-5-[2-(4-quinolonyl)]pyrido[2,3-d]pyrimidine]-3-acetate, 2,4(1H,3H)-dioxo-6-ethoxycarbonyl-7-isopropyl-1-(2-methoxybenzyl)-5-[2-(4-quinolonyl)]pyrido[2,3-d]pyrimidine-3-acetic acid, 2,4(1H,3H)-dioxo-6-isobutoxycarbonyl-7-isopropyl-1-(2-methoxybenzyl)-5-(2-quinolylpyrido[2,3-d]pyrimidine-3-acetic acid, 2,4(1H,3H)-dioxo-6-ethoxycarbonyl-7-isopropyl-1-(2-methoxybenzyl)-5-(2-quinolylpyrido[2,3-d]pyrimidine-3-acetic acid, 2,4(1H,3H)-dioxo-6-cyanoethoxycarbonyl-7-isopropyl-1-(2-methoxybenzyl)-5-(2-quinolylpyrido[2,3-d]pyrimidine-3-acetic acid, and ethyl[2,4(1H,3H)-dioxo-6-carboxy-7-isopropyl-1-(2-methylthiobenzyl)-5-[2-(4-quinolonyl)]pyrido[2,3-d]pyrimidine-3-acetate;

or a salt thereof.

8. A pharmaceutical composition useful as an endothelin receptor antagonist comprising, as the effective component, at least one compound selected from pyrido[2,3-d]pyrimidine derivative represented by the formula (A) as claimed in claim 1 or a pharmaceutically acceptable salt thereof.

9. A pharmaceutical composition as claimed in claim 8, wherein the antagonist is an endothelin-A receptor antagonist.

10. A method for treating a patient suffering from myocardial infarction which comprises administering to said patient an effective daily dosage of between 0.1 and 500 mg per day of the pyrido[2,3-d]pyrimidine derivative of claim 1 or a pharmaceutically acceptable salt thereof in the form of a pharmaceutical composition containing the derivative as the active component.

11. A pharmaceutical composition as claimed in claim 9 wherein the antagonist is a therapeutic agent for myocardial infarction.

12. A method for treating a patient suffering from myocardial infarction which comprises administering to said patient an effective daily dosage of between 0.1 and 500 mg per day of the composition of claim 9.

13. A pyrido[2,3-d]pyrimidine derivative represented by the formula (A'''):

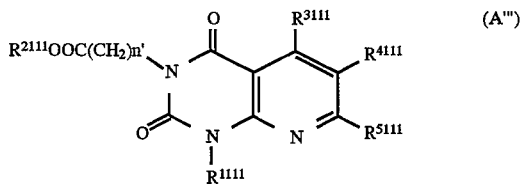

wherein n'' denotes an integer of 1 to 3;

$R^{1111}$ is a phenyl-$C_{1-3}$ alkyl group optionally substituted by at least one member selected from the group consisting of a $C_{1-6}$ alkoxy group and a $C_{1-6}$ alkylthio group;

$R^{2111}$ is a hydrogen atom or a $C_{1-6}$ alkyl group;

$R^{3111}$ is a quinolyl group or quinolonyl group;

$R^{4111}$ is a group of the formula: —COOR$^{611}$ wherein R$^{611}$ is a hydrogen atom or a $C_{1-6}$ alkyl group optionally substituted by a cyano group; and $R^{5111}$ is a $C_{1-6}$ alkyl group;

or a salt thereof.

* * * * *